United States Patent [19]

Schaefer

[11] 4,311,700
[45] Jan. 19, 1982

[54] PYRIMIDOBENZODIAZEPINONES, THEIR USE AND MEDICAMENTS CONTAINING THEM

[75] Inventor: Hartmann Schaefer, Constance, Fed. Rep. of Germany

[73] Assignee: BYK Gulden Lomberg Chemische Fabrik GmbH, Constance, Fed. Rep. of Germany

[21] Appl. No.: 175,243

[22] Filed: Aug. 4, 1980

[30] Foreign Application Priority Data

Aug. 10, 1979 [CH] Switzerland ............................ 7334/79
Aug. 10, 1979 [CH] Switzerland ............................ 7335/79

[51] Int. Cl.³ ................ C07D 487/04; A61K 31/505; A61K 31/55
[52] U.S. Cl. .............................. 424/248.54; 424/250; 424/251; 424/244; 260/239.3 T
[58] Field of Search ................. 260/239.3 T; 424/250, 424/251, 244, 248.54

[56] References Cited

U.S. PATENT DOCUMENTS 4,021,557  5/1977  Schmidt ............................. 424/256

FOREIGN PATENT DOCUMENTS 2707270  8/1978  Fed. Rep. of Germany .

OTHER PUBLICATIONS

Ina et al., "Yakugaku Zasshi", vol. 98, No. 1, January 1978, pp. 72–76 (J. Pharmaceutical Soc. of Japan).

*Primary Examiner*—Robert T. Bond
*Attorney, Agent, or Firm*—Berman, Aisenberg & Platt

[57] ABSTRACT

11-Acyl-2-phenyl- and 11-acyl-5,6-dihydropyrimido[4,5-b][1,5]benzodiazepin-5-ones, their acid-addition salts and their N-oxides provide protective action for the stomach and intestines of warm-blooded animals and inhibit the formation of gastric and intestinal ulcers.

25 Claims, No Drawings

PYRIMIDOBENZODIAZEPINONES, THEIR USE AND MEDICAMENTS CONTAINING THEM

TECHNICAL FIELD

The invention relates to a select class of benzodiazepinones, a process for their preparation, their use and medicaments containing them.

BACKGROUND

Pyridobenzodiazepinones are said to possess antiulcerogenic, secreto-inhibitory, antitussive and, to some extent, anti-emetic activity (U.S. Pat. Nos. 3,660,380 and 3,743,734), and are said to be antitussives (DE-AS No. 16 20 523).

Pyrimidobenzodiazepines are said to be useful for treating hypoxia and are said to possess hypothermal, antipyretic and anti-inflammatory activity (U.S. Pat. Nos. 3,872,122 and 3,880,855). Pyrimido[4,5-b][1,5]benzodiazepin-5-one is described, but no biological properties of this compound are disclosed [K. J. M. Andrews, B. P. Tong, *J. Chem. Soc.* 1753 (1968)].

SUMMARY OF THE INVENTION

A new class of pyrimidobenzodiazepinones, which is neither mentioned in nor obvious from the aforesaid publications, has now been synthesized. This new class of pyrimidobenzodiazepinones possesses interesting and particularly advantageous pharmacological properties. The compounds are useful in the pharmaceutical industry as active ingredients, as intermediate products and for preparing medicaments.

The new class of compounds comprises the following free bases:

(a) 11-halo(lower)alkylcarbonyl-5,6-dihydropyrimido[4,5-b][1,5]benzodiazepin-5-ones,
(b) 11-halo(lower)alkylcarbonyl-6-(lower)alkyl-5,6-dihydropyrimido[4,5-b][1,5]benzodiazepin-5-ones,
(c) 11-(disubstituted)aminoalkylcarbonyl-5,6-dihydropyrimido[4,5-b][1,5]benzodiazepin-5-ones,
(d) 11-(disubstituted)aminoalkylcarbonyl-6(lower)alkyl-5,6-dihydropyrimido[4,5-b][1,5]benzodiazepin-5-ones,
(e) 11-halo(lower)alkylcarbonyl-2-phenyl-5,6-dihydropyrimido[4,5-b][1,5]benzodiazepin-5-ones,
(f) 11-halo(lower)alkylcarbonyl-6-(lower)alkyl-2-phenyl-5,6-dihydropyrimido[4,5-b][1,5]benzodiazepin-5-ones,
(g) 11-(disubstituted)aminoalkylcarbonyl-2-phenyl-5,6-dihydropyrimido[4,5-b][1,5]benzodiazepin-5-ones,
(h) 11-(disubstituted)aminoalkylcarbonyl-6-(lower)alkyl-2-phenyl-5,6-dihydropyrimido[4,5-b][1,5]-benzodiazepin-5-ones,
(i) 6-(lower)alkyl-2-phenyl-5,6-dihydropyrimido[4,5-b][1,5]benzodiazepin-5-ones,
(j) 2-phenyl-5,6-dihydropyrimido[4,5-b][1,5]benzodiazepin-5-one their acid-addition salts (particularly those which are pharmacologically acceptable) and N-oxides of both the free bases and the acid-addition salts.

DETAILS

These compounds are benzodiazepinones of the formula

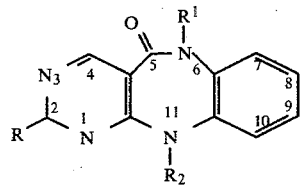

wherein
R denotes a hydrogen atom (—H) or a phenyl group,
$R^1$ denotes a hydrogen atom (—H) or an alkyl radical with from 1 to 4 carbon atoms,
$R^2$ denotes —CO—$C_nH_{2n}$—$R^3$ or (when R is a phenyl group) a hydrogen atom (—H),
$R^3$ denotes halo or —N($R^4$)$R^5$,
$R^4$ denotes an alkyl radical with from 1 to 4 carbon atoms, an alkenyl radical with from 3 to 5 carbon atoms, or, together with $R^5$ and the nitrogen atom to which both are bound, a pyrrolidino, piperidino, morpholino or perhydroazepino radical, a piperazino radical which is optionally substituted in the 4-position by a methyl, ethyl or benzyl group or a homopiperazino radical which is optionally substituted in the 4-position by a methyl group,
$R^5$ denotes an alkyl radical with from 1 to 4 carbon atoms, which is optionally substituted by a dialkylamino group with from 1 to 4 carbon atoms in each alkyl radical, an alkenyl radical with from 3 to 5 carbon atoms or, together with $R^4$ and the nitrogen atom to which both are bound, a pyrrolidino, piperidino, morpholino or perhydroazepino radical, a piperazino radical which is optionally substituted in the 4-position by a methyl, ethyl or benzyl group or a homopiperazino radical which is optionally substituted in the 4-position by a methyl group, and
n represents 1 or 2, their N-oxides and their acid-addition salts with inorganic or organic acids.

Alkyl radicals with from 1 to 4 carbon atoms are methyl, ethyl, propyl, butyl, isopropyl, isobutyl, sec.-butyl and tert.-butyl.

Alkenyl radicals with from 3 to 5 carbon atoms are, e.g., allyl and 2-methylallyl.

Halo is chloro, bromo and iodo, preferably chloro and bromo, especially chloro.

Suitable salts include all acid-addition salts. Particular attention is accorded the pharmacologically-acceptable salts of the inorganic and organic acids customarily used in medicine. Pharmacologically-unacceptable salts are also useful, since they are readily converted into pharmacologically-acceptable salts by conventional processes. Suitable examples of the latter are water-soluble and water-insoluble acid-addition salts, such as the hydrochloride, hydrobromide, hydroiodide, phosphate, nitrate, sulfate, acetate, citrate, gluconate, benzoate, hibenzate {[2-(4-hydroxybenzoyl)]benzoate}, fendizoate {o-[2'-hydroxy-4-biphenylyl)carbonyl]benzoate}, propionate, butyrate, sulfosalicylate, maleate, laurate, malate, fumarate, succinate, oxalate, tartrate, amsonate (4,4'-diaminostilbene-2,2'-disulfonate), embonate (4,4'-methylene-bis-3-hydroxy-2-naphthoate), metembonate (4,4'-methylene-bis-3-methoxy-2-naphthoate), stearate, tosylate (p-toluenesulfonate), 2-hydroxy-3-naphthoate, 3-hydroxy-2-naphthoate and mesylate (methansulfonate).

Benzodiazepinones Ia of formula I, wherein

R denotes a phenyl group,

R$^1$ denotes a hydrogen atom (—H) or an alkyl radical with from 1 to 4 carbon atoms, R$^2$ denotes —CO—C$_n$H$_{2n}$—R$^3$ R$^3$ denotes —N(R$^4$)R$^5$, R$^4$ denotes an alkyl radical with from 1 to 4 carbon atoms, an alkenyl radical with from 3 to 5 carbon atoms or, together with R$^5$ and the nitrogen atom to which both are bound, a pyrrolidino, piperidino, morpholino or perhydroazepino radical, a piperazino radical which is optionally substituted in the 4-position by a methyl, ethyl or benzyl group or a homopiperazino radical which is optionally substituted in the 4-position by a methyl group, R$^5$ denotes an alkyl radical with from 1 to 4 carbon atoms, which is optionally substituted by a dialkylamino group with from 1 to 4 carbon atoms in each alkyl radical, an alkenyl radical with from 3 to 5 carbon atoms or, together with R$^4$ and the nitrogen atom to which both are bound, a pyrrolidino, piperidino, morpholino or perhydroazepino radical, a piperazino radical which is optionally substituted in the 4-position by a methyl, ethyl or benzyl group or a homopiperazino radical which is optionally substituted in the 4-position by a methyl group, and n represents 1 or 2, and their N-oxides and their acid-addition salts with inorganic or organic acids form one embodiment of the invention.

Preferred representatives of embodiment Ia are those in which R$^1$ denotes an alkyl radical with 1 to 4 carbon atoms, R$^4$ denotes an alkyl radical with from 1 to 4 carbon atoms, R$^5$ denotes an alkyl radical with from 1 to 4 carbon atoms (which is substituted by a dialkylamino group with from 1 to 4 carbon atoms in each alkyl radical), or R$^4$ and R$^5$ (together with the nitrogen atom to which both are bound) denote a pyrrolidino, piperidino or morpholino radical, or a piperazino radical which is substituted in the 4-position by a methyl group, and n represents 1; and their pharmacologically-compatible acid-addition salts.

Particularly preferred representatives of the embodiment Ia are those in which R$^1$ denotes a methyl, propyl, isopropyl, n-butyl or sec.-butyl group, R$^4$ denotes a methyl group, R$^5$ denotes a 2-dimethylaminoethyl group, or R$^4$ and R$^5$ (together with the nitrogen atom to which both are bound) denote a pyrrolidino, piperidino or N-methylpiperazino group, and n represents 1; and their pharmacologically-compatible acid-addition salts.

Benzodiazepinones Ib of formula I, wherein

R denotes a phenyl group,

R$^1$ denotes a hydrogen atom (—H) or an alkyl radical with from 1 to 4 carbon atoms, R$^2$ denotes a hydrogen atom (—H) or —CO—C$_n$H$_{2n}$—R$^3$, R$^3$ denotes halo and n represents 1 or 2 and their N-oxides and their acid-addition salts with inorganic or organic acids form a second embodiment of the invention.

Preferred representatives of embodiment Ib are those in which R$^1$ denotes an alkyl radical with from 1 to 4 carbon atoms, R$^3$ denotes chloro or bromo and n represents 1; and their acid-addition salts.

Particularly preferred representatives of embodiment Ib are those in which R$^1$ denotes a methyl, propyl, isopropyl, n-butyl or sec.-butyl group, R$^3$ denotes chloro and n represents 1; and their acid addition salts.

Benzodiazepinones Ic of formula I, wherein

R denotes a hydrogen atom (—H),

R$^1$ denotes a hydrogen atom (—H) or an alkyl radical with from 1 to 4 carbon atoms, R$^2$ denotes —CO—C$_n$H$_{2n}$—R$^3$, R$^3$ denotes —N(R$^4$)R$^5$, R$^4$ denotes an alkyl radical with from 1 to 4 carbon atoms, an alkenyl radical with from 3 to 5 carbon atoms, or, together with R$^5$ and the nitrogen atom to which both are bound, a pyrrolidino, piperidino, morpholino or perhydroazepino radical, a piperazino radical which is optionally substituted in the 4-position by a methyl, ethyl or benzyl group or a homopiperazino radical which is optionally substituted in the 4-position by a methyl group, and R$^5$ denotes an alkyl radical with from 1 to 4 carbon atoms, which is optionally substituted by a dialkylamino group with from 1 to 4 carbon atoms in each alkyl radical, an alkenyl radical with from 3 to 5 carbon atoms or, together with R$^4$ and the nitrogen atom to which both are bound, a pyrrolidino, piperidino, morpholino or perhydroazepino radical, a piperazino radical which is optionally substituted in the 4-position by a methyl, ethyl or benzyl group or a homopiperazino radical which is optionally substituted in the 4-position by a methyl group, and n represents 1 or 2, their N-oxides and their acid-addition salts with inorganic or organic acids form a third embodiment of the invention.

Preferred representatives of embodiment Ic are those in which R$^4$ and R$^5$ (together with the nitrogen atom to which both are bound) denote a pyrrolidino, piperidino or morpholino radical or a piperazino radical which is substituted in the 4-position by a methyl group, and n represents 1; and their pharmacologically-compatible acid-addition salts.

Particularly preferred representatives of embodiment Ic are those in which R$^1$ denotes a hydrogen atom or a methyl or n-butyl group, R$^4$ and R$^5$ (together with the nitrogen atom to which both are bound) denote a piperidino, morpholino or N-methylpiperazino group, and n represents 1; and their pharmacologically-compatible acid addition salts.

Benzodiazepinones Id of formula I, wherein

R denotes a hydrogen atom (—H),

R$^1$ denotes a hydrogen atom (—H) or an alkyl radical with from 1 to 4 carbon atoms, R$^2$ denotes —CO—C$_n$H$_{2n}$—R$^3$, R$^3$ denotes halo and n represents 1 or 2, their N-oxides and their acid-addition salts with inorganic or organic acids form a fourth embodiment of the invention.

Preferred representatives of embodiment Id are those in which R$^3$ denotes chloro or bromo and n represents 1, and their acid-addition salts.

Particularly preferred representatives of embodiment Id are those in which R$^1$ denotes a hydrogen atom or a methyl or n-butyl group, R$^3$ denotes chloro and n represents 1; and their acid-addition salts.

The following compounds are illustrative examples of the invention:

6-isopropyl-11-[(4-methyl-1-piperazinyl)acetyl]-2-phenyl-5,6-dihydropyrimido[4,5-b][1,5]benzodiazepin-5-one, 6-butyl-11-diallylaminoacetyl-2-phenyl-5,6-dihydropyrimido[4,5-b][1,5]benzodiazepin-5-one, 6-methyl-11-pyrrolidinoacetyl-2-phenyl-5,6-dihydropyrimido[4,5-b][1,5]benzodiazepin-5-one,
6-(tert.-butyl)-11-(2-morpholinopropionyl)-2-phenyl-5,6-dihydropyrimido[4,5-b][1,5]benzodiazepin-5-one,
6-methyl-11-(3-homopiperazinopropionyl)-5,6-dihydropyrimido[4,5-b][1,5]benzodiazepin-5-one,
6-ethyl-2-phenyl-11-piperazinoacetyl-5,6-dihydropyrimido[4,5-b][1,5]benzodiazepin-5-one,
6-ethyl-11-diisopropylaminoacetyl-2-phenyl-5,6-dihydropyrimido[4,5-b][1,5]benzodiazepin-5-one,
6-propyl-11-[(4-ethyl-1-piperazinyl)acetyl]-2-phenyl-5,6-dihydropyrimido[4,5-b][1,5]benzodiazepin-5-one,
6-methyl-11-perhydroazepinoacetyl-2-phenyl-5,6-dihydropyrimido[4,5-b][1,5]benzodiazepin-5-one,
6-isopropyl-11-piperidinoacetyl-2-phenyl-5,6-dihydropyrimido[4,5-b][1,5]benzodiazepin-5-one,
6-ethyl-11-[N-(n-butyl)-N-(tert.-butyl)amino]acetyl-2-phenyl-5,6-dihydropyrimido[4,5-b][1,5]benzodiazepin-5-one,
6-butyl-11-dibutylaminoacetyl-2-phenyl-5,6-dihydropyrimido[4,5-b][1,5]benzodiazepin-5-one,
6-isobutyl-11-[(4-methyl-1-piperazinyl)acetyl]-2-phenyl-5,6-dihydropyrimido[4,5-b][1,5]benzodiazepin-5-one
6-(sec.-butyl)-11-[(4-methyl-1-piperazinyl)acetyl]-2-phenyl-5,6-dihydropyrimido[4,5-b][1,5]benzodiazepin-5-one,
6-methyl-11-dimethylaminoacetyl-2-phenyl-5,6-dihydropyrimido[4,5-b][1,5]benzodiazepin-5-one,
6-isopropyl-11-perhydroazepinoacetyl-2-phenyl-5,6-dihydropyrimido[4,5-b][1,5]benzodiazepin-5-one,
6-isobutyl-11-(4-methylhomopiperazino)acetyl-2-phenyl-5,6-dihydropyrimido[4,5-b][1,5]benzodiazepin-5-one,
11-[N-(diethylaminomethyl)-N-ethylamino]acetyl-6-ethyl-2-phenyl-5,6-dihydropyrimido[4,5-b][1,5]benzodiazepin-5-one,
6-ethyl-11-[N-(n-butyl)-N-(tert.-butyl)amino]acetyl-5,6-dihydropyrimido[4,5-b][1,5]benzodiazepin-5-one,
6-(n-butyl)-11-di-(n-butyl)aminoacetyl-5,6-dihydropyrimido[4,5-b][1,5]benzodiazepin-5-one,
11-[(4-methyl-1-piperazinyl)acetyl]-5,6-dihydropyrimido[4,5-b][1,5]benzodiazepin-5-one,
6-methyl-11-[(4-methyl-1-piperazinyl)acetyl]-5,6-dihydropyrimido[4,5-b][1,5]benzodiazepin-5-one,
6-(sec.-butyl)-11-[(4-methyl-1-piperazinyl)acetyl]-5,6-dihydropyrimido[4,5-b][1,5]benzodiazepin-5-one,
6-methyl-11-dimethylaminoacetyl-5,6-dihydropyrimido-[4,5-b][1,5]benzodiazepin-5-one,
11-perhydroazepinoacetyl-5,6-dihydropyrimido[4,5-b][1,5]benzodiazepin-5-one,
11-diallylaminoacetyl-5,6-dihydropyrimido[4,5-b][1,5]benzodiazepin-5-one,
6-methyl-11-pyrrolidinoacetyl-5,6-dihydropyrimido[4,5-b][1,5]benzodiazepin-5-one,
6-ethyl-11-diisopropylaminoacetyl-5,6-dihydropyrimido[4,5-b][1,5]benzodiazepin-5-one,
11-[(4-ethyl-1-piperazinyl)acetyl]-5,6-dihydropyrimido[4,5-b][1,5]benzodiazepin-5-one,
6-methyl-11-perhydroazepinoacetyl-5,6-dihydropyrimido[4,5-b][1,5]benzodiazepin-5-one and
6-isopropyl-11-piperidinoacetyl-5,6-dihydropyrimido[4,5-b][1,5]benzodiazepin-5-one,
their N-oxides and their acid-addition salts, especially
6-methyl-11-[(4-methyl-1-piperazinyl)acetyl]-2-phenyl-5,6-dihydropyrimido[4,5-b][1,5]benzodiazepin-5-one,
11-[N-(2-dimethylaminoethyl)-N-methylamino]acetyl-6-methyl-2-phenyl-5,6-dihydropyrimido[4,5-b][1,5]benzodiazepin-5-one,
6-methyl-2-phenyl-11-pyrrolidinoacetyl-5,6-dihydropyrimido[4,5-b][1,5]benzodiazepin-5-one,
11-[(4-methyl-1-piperazinyl)acetyl]-5,6-dihydropyrimido[4,5-b][1,5]benzodiazepin-5-one,
6-methyl-2-phenyl-11-piperidinoacetyl-5,6-dihydropyrimido[4,5-b][1,5]benzodiazepin-5-one,
6-isopropyl-2-phenyl-11-[(4-methyl-1-piperazinyl)acetyl]5,6-dihydropyrimido[4,5-b][1,5]benzodiazepin-5-one,
6-(n-butyl)-11-[(4-methyl-1-piperazinyl)acetyl]-5,6-dihydropyrimido[4,5-b][1,5]benzodiazepin-5-one and
6-(sec.-butyl)-2-phenyl-11-[(4-methyl-1-piperazinyl)acetyl]5,6-dihydropyrimido[4,5-b][1,5]benzodiazepin-5-one
and their acid-addition salts.

The benzodiazepinones of formula I, those of embodiments Ia, Ib, Ic, Id, their N-oxides and their acid-addition salts possess valuable properties which make them industrially useful.

The benzodiazepinones of formula I, in which $R^2$ denotes $-CO-C_nH_{2n}-R^3$, $R^3$ denotes $-N(R^4)R^5$ and R, $R^1$, $R^4$, $R^5$ and n have their previously-ascribed meanings, the benzodiazepinones Ia and Ic, and N-oxides and acid-addition salts of these compounds are pharmacologically-active compounds according to the invention and are characterized by imparting excellent protective action on the stomach and on the intestines of warm-blood animals; they inhibit, in particular, formation of gastric and intestinal ulcers.

In addition, owing to low toxicity and the absence of appreciable side-effects, they have an advantageous therapeutic range. Moreover, these compounds have only a slight anticholinergic action as can be determined by the slight inhibition of the salivation induced by carbachol. The benzodiazepinones (according to the invention) of formula I in which $R^2$ denotes a hydrogen atom (—H) or the group $-CO-C_nH_{2n}-R^3$ and $R^3$ denotes a halogen atom, and benzodiazepinones Ib and Id are valuable intermediate products for preparing the pharmacologically-active compounds according to the invention. The excellent effectiveness of the pharmacologically-active benzodiazepinones and their pharmacologically-acceptable N-oxides and corresponding acid-addition salts makes it possible to employ them in human or veterinary medicine, wherein they are used for the treatment and prophylaxis of diseases due to affections of the stomach and intestines. For example, in humans or animals acute and chronic *Ulcus ventriculi* and *Ulcus duodeni*, gastritis, hyperacid irritated stomach and stomach complaints caused by medicaments are treated with these compounds.

The invention also relates, therefore, to a process for treating mammals which are affected by one of the noted ailments. The process is characterized by administering a therapeutically-effective and pharmacologically-acceptable amount of one or more of the previously-mentioned pharmacologically-active compounds to an affected animal.

The invention relates, in addition, to the use of the compounds according to the invention in combating the indicated diseases. The invention likewise includes the use of the compounds in the preparation of medicaments which are employed for combating the noted diseases.

The invention also relates to medicaments which contain one or more benzodiazepinones of formula I, wherein R denotes a hydrogen atom (—H) or a phenyl group, $R^1$ denotes a hydrogen atom (—H) or an alkyl radical with from 1 to 4 carbon atoms, $R^2$ denotes —CO—$C_nH_{2n}$—$R^3$, $R^3$ denotes —N($R^4$)$R^5$, $R^4$ denotes an alkyl radical with from 1 to 4 carbon atoms or an alkenyl radical with from 3 to 5 carbon atoms, $R^5$ denotes an alkyl radical with from 1 to 4 carbon atoms (optionally substituted by a dialkylamino group with from 1 to 4 carbon atoms in each alkyl radical) or an alkenyl radical with from 3 to 5 carbon atoms, or $R^4$ and $R^5$ together, and including the nitrogen atom to which both are bound, denote a pyrrolidino, piperidino, morpholino or perhydroazepino radical, a piperazino radical (optionally substituted in the 4-position by a methyl, ethyl or benzyl group) or a homopiperazino radical (optionally substituted in the 4-position by a methyl group), and n represents 1 or 2, and/or their pharmacologically-acceptable N-oxides and/or corresponding pharmacologically-acceptable acid-addition salts.

Embodiments of the medicaments are those which contain benzodiazepinones Ia or Ic and/or their pharmacologically-acceptable N-oxides and/or corresponding acid-addition salts, or which contain their preferred or particularly preferred representatives and/or pharmacologically-acceptable acid-addition salts thereof.

The medicaments are prepared by known processes with conventional additives. The new compounds are employed as such or, if appropriate, in combination with suitable pharmaceutical excipients. When new pharmaceutical formulations contain pharmaceutical excipients in addition to the active compounds, the active-compound content in such mixtures is from 0.5 to 95, preferably from 15 to 75, percent by weight of the total mixture.

The active compounds are used in any formulation which is suitable to establish and/or maintain a sufficient blood or tissue level of active compound. This is achieved, for example, by oral, rectal or parenteral administration in suitable doses. The pharmaceutical formulation of active compound is usually in the form of a unit dose appropriate for the desired administration. A unit dose is, for example, in the form of a tablet, a dragee, a capsule, a suppository or a measured volume of a powder, of a granular material, of a solution, of an emulsion or of a suspension.

"Unit dose", for the purpose of the present invention, means a physically-determined unit which contains an individual amount of the active ingredient in combination with a pharmaceutical excipient, the content of active compound in the unit dose corresponding to a fraction or a multiple of a therapeutic individual dose. An individual dose preferably contains the amount of active compound which is given in one administration and usually corresponds to a whole daily dose or a half, one-third or one-quarter of the daily dose. If only a fraction, such as a half or one quarter, of the unit dose is required for an individual therapeutic administration, the unit dose is advantageously divisible, for example in the form of a tablet with a breaking groove.

When in the form of unit doses and intended, for example, for administration to humans, the pharmaceutical formulations according to the invention contain from about 1 to 300 mg, advantageously from 5 to 100 mg, and, in particular, from 10 to 50 mg, of active compound.

In general, it is advantageous in human medicine to administer the active compound or compounds, when these are given orally, in a daily dose of from 0.01 to 12, preferably from 0.07 to 4 and, in particular from 0.15 to 2, mg/kg of body weight, if appropriate in the form of several, preferably 1 to 3, individual administrations to achieve the desired results. An individual administration contains the active compound or compounds in amounts of from 0.01 to 4, preferably from 0.07 to 1.4 and, in particular, from 0.15 to 0.7, mg/kg of body weight. Similar dosages are used in parenteral, for example intravenous, treatment.

The pharmaceutical formulation is administered, for therapeutic purposes, from 1 to 4 times daily, at fixed or varying points in time, for example before each meal and/or in the evening. It is, however, sometimes necessary to deviate from the indicated dosages and, in particular, to do so in accordance with the nature, body weight and age of the patient under treatment, the nature and severity of the illness, the actual constitution of the formulation, the application of the medicament, frequency of administration and also the time or interval over which administration takes place. Thus, in some cases it is sufficient to manage with less than the previously-mentioned amount of active compound, while in other cases it is necessary to exceed the noted amount of active compound. In acute cases, a higher dose is administered at the start of treatment. After desired action has taken place, the dose is reduced to a lower level.

The optimum dosage and method of administration of active compounds required in each particular case is readily determined by any expert, in accordance with his expert knowledge.

The pharmaceutical formulations generally comprise active compound (according to the invention) and non-toxic, pharmaceutically-acceptable medicinal excipients (used as an admixture or diluent in solid, semisolid or liquid form, or as a means of encasing, for example in the form of a capsule, a tablet coating, a sachet or other container for the therapeutically-active ingredient). An excipient, for example, optionally serves as a promoter of resorption of the medicament by the body, as a formulating auxiliary, as a sweetener, as a flavor correctant, as a colorant or as a preservative.

Examples of orally-used forms are tablets, dragees, hard and soft capsules (for example, made of gelatin), dispersible powders, granules, aqueous and oily suspensions, emulsions, solutions or syrups.

Tablets optionally contain inert diluents, for example calcium carbonate, calcium phosphate, sodium phosphate or lactose; granulating agents and dispersing agents, for example maize starch or alginates; binders, for example starch, gelatin or gum acacia; and lubricants, for example aluminum stearate or magnesium stearate, talc or silicone oil. The tablets are also optionally provided with a coating, such as one for delayed dissolution and resorption of the medicament in the gastro-intestinal tract, and hence, for example, better toleration, a protracted effect or a retarded effect is achieved. Gelatin capsules contain, e.g., the medicament mixed with a solid diluent, for example calcium carbonate or kaolin, or an oily diluent, for example olive oil, groundnut oil or paraffin oil.

Aqueous suspensions, which, if appropriate, are prepared for a short period; they contain, e.g., suspending agents, for example sodium carboxymethylcellulose, methylcellulose, hydroxypropylcellulose, sodium alginate, polyvinylpyrrolidone, gum tragacanth or gum acacia; dispersing agents and wetting agents, for example polyoxyethylene (stearate, heptadecaethyleneoxycetanol, polyoxyethylene) sorbitol monooleate, polyoxyethylene sorbitan monooleate or lecithin; preservatives, for example methyl hydroxybenzoate or propyl hydroxybenzoate; flavoring agents; and sweeteners, for example sucrose, lactose, sodium cyclamate, dextrose or invert sugar syrup.

Oily suspensions contain, for example, groundnut oil, olive oil, sesame oil, coconut oil or paraffin oil; thickeners, such as beeswax, hard paraffin or cetyl alcohol; and also sweeteners, flavoring agents and antioxidants.

Water-dispersible powders and granules contain the medicaments mixed with dispersing agents, wetting agents and suspending agents, for example those previously mentioned, as well as with sweeteners, flavoring agents and colorants.

Emulsions contain, for example, olive oil, groundnut oil or paraffin oil, in addition to emulsifying agents, such as gum acacia, gum tragacanth, phosphatides, sorbitan monooleate or polyoxyethylene sorbitan monooleate, sweeteners and flavorings.

Suppositories, prepared with the aid of binders which melt at rectal temperature, for example cocoa butter or polyethylene glycol, are used for rectal administration of the medicaments.

Sterile injectable aqueous solutions, which, if appropriate, are prepared for a short period, with isotonic-salt solutions or other solutions which contain dispersing agents or wetting agents and/or pharmacologically-acceptable diluents, for example propylene glycol or butylene glycol, are used for parenteral administration of the medicaments.

Oral administration of the medicaments is preferred.

The active compound or compounds are also, optionally, in a micro-encapsulated form, if appropriate together with one or more of the indicated excipients or additives.

When the pharmacologically-active compounds according to the invention and/or their N-oxides and/or their acid-addition salts are employed for the treatment of previously-mentioned diseases, the pharmaceutical formulations optionally contain one or more other pharmacologically-active ingredients from other groups of medicaments, such as antacids, for example aluminum hydroxide or magnesium aluminate; tranquillizers, such as benzodiazepines, for example diazepam; spasmolytic agents, such as bietamiverine or camylofin; anticholinergic agents, such as oxyphencyclimin or phencarbamide; local anaesthetics, such as tetracaine or procaine; and, if appropriate, also ferments, vitamins, aminoacids, etc.

The invention also relates to a process for preparing benzodiazepinones of formula I, wherein R denotes a hydrogen atom or a phenyl group,
$R^1$ denotes a hydrogen atom or an alkyl radical with from 1 to 4 carbon atoms,
$R^2$ denotes $-CO-C_nH_{2n}-R^3$,
$R^3$ denotes halo (a halogen atom) or $-N(R^4)R^5$,
$R^4$ denotes an alkyl radical with from 1 to 4 carbon atoms, or an alkenyl radical with from 3 to 5 carbon atoms,
$R^5$ denotes an alkyl radical with 1 to 4 carbon atoms (which may be substituted by a dialkylamino group with from 1 to 4 carbon atoms in each alkyl radical), or an alkenyl radical with from 3 to 5 carbon atoms, or
$R^4$ and $R^5$ together, and including the nitrogen atom to which both are bound, denote a pyrrolidino, piperidino, morpholino or perhydroazepino radical or a piperazino radical which is optionally substituted in the 4-position by a methyl, ethyl or benzyl group or a homopiperazino radical which is optionally substituted in the 4-position by a methyl group and
n represents 1 or 2, and their N-oxides and their acid-addition salts with inorganic and organize acids. The process is characterized by reacting a benzodiazepinone of the formula (II)

wherein R and $R^1$ have their previously-ascribed meanings, with a compound of the formula $$Z-\underset{\underset{O}{\|}}{C}-C_nH_{2n}-X \qquad (III)$$

wherein
n has its previously-stated meaning,
X represents halo and
Z represents a leaving group.

The thus-obtained product is then optionally reacted with an amine of the formula $$H-N\diagup_{R^5}^{R^4} \qquad (IV)$$

wherein $R^4$ and $R^5$ have their previously-noted meanings, and, if appropriate, the resulting product is optionally converted into an N-oxide and/or an acid-addition salt. The reaction of benzodiazepinones II with compounds III is carried out in a conventional and well established manner.

The leaving group Z is, for example, a halogen atom, especially a chlorine atom, or the group $X-C_nH_{2n}-CO-O-$. When Z is a halogen atom, it is expedient to carry out the reaction in the presence of an acid-binding agent (proton acceptor). Examples of suitable acid-binding agents are alkali-metal carbonates or bicarbonates, such as sodium carbonate or potassium bicarbonate; or tertiary amines, such as pyridine, triethylamine or ethyl diisopropylamine.

It is expedient to carry out the reaction in inert, anhydrous solvents. The following are examples of suitable solvents: chlorinated hydrocarbons, for example methylene chloride or chloroform; open-chain or cyclic ethers, for example diethyl ether, diethylene glycol dimethyl ether, tetrahydrofuran or, in particular, dioxan; and aromatic hydrocarbons, for example benzene or toluene.

Depending on the nature of the leaving group, the proton acceptor and the reactants, the reaction temperature is between 20° and 150° C., in particular between 60° and 110° C., preferably the boiling point of the solvent used. The reaction time is between 20 minutes and 60 hours.

The reaction of II with III leads to benzodiazepinones I, wherein $R^3$ is a halogen atom ($R^3=X$). The embodiments Ib and Id are prepared by similar reactions of compounds IIb, IId, IIIb and IIId, respectively, wherein the substituents R, $R^1$, and n have corresponding meanings. These compounds I (with $R^3=X$), Ib and Id are valuable intermediates.

The optionally-desired following reaction of these intermediates with amines IV, IVa or IVc, respectively, wherein the substituents $R^4$ and $R^5$ have corresponding meanings, leads to benzodiazepinones I, wherein $R^3$ denotes the group $—N(R^4)R^5$, or to benzodiazepinones Ia or Ic, repectively.

The reaction of the intermediates with amines IV is carried out in a conventional manner. It is expediently carried out in the presence of an acid-binding agent (proton acceptor). Examples of suitable acid-binding agents are alkali-metal carbonates or bicarbonates, such as sodium carbonate, potassium carbonate or sodium bicarbonate; or tertiary amines, such as pyridine, triethylamine or ethyl diisopropylamine. In order to avoid side reactions, it is expedient to use the compound IV as the proton acceptor. In this case, the reaction is carried out with, for example, a 2-fold to 5-fold excess of IV.

The reaction is carried out in a suitable, expediently inert, anhydrous solvent, such as a lower alcohol, for example methanol, ethanol or isopropanol; or an open-chain or cyclic ether, for example tetrahydrofuran or preferably dioxan; or an aromatic hydrocarbon, such as benzene or preferably toluene; or a chlorinated hydrocarbon, such as methylene chloride.

The reaction temperature is from 0° to 150° C., in particular from 50° to 110° C., preferably the boiling point of the solvent used. Depending on the nature of the amine used, the reaction time is between some minutes and several hours; in some cases the reaction is accelerated by adding alkalimetal iodide. When readily-volatile amines are used, it is expedient to carry out the reaction at a low temperature or in a closed vessel.

Acid-addition salts are obtained by dissolving the free bases in a suitable solvent, for example in a chlorinated hydrocarbon, such as methylene chloride or chloroform, or a low-molecular aliphatic alcohol (ethanol or isopropanol), which contains the desired acid or to which the desired acid is subsequently added. The salts are isolated by filtration, reprecipitation or precipitation with a non-solvent for the addition salt or by evaporating the solvent.

Resulting salts are converted (by being rendered alkaline, for example, with aqueous sodium bicarbonate) into free bases, which are, in turn, converted into acid-addition salts. Pharmacologically-unacceptable acid-addition salts are converted in this manner into pharmacologically-acceptable acid-addition salts.

N-Oxides are obtained by oxidizing the benzodiazepinones with suitable oxidizing agents, such as peroxide compounds, for example hydrogen peroxide or m-chloroperoxybenzoic acid, in suitable inert solvent, for example methylene chloride, in a manner known to the expert (see also Houben-Weyl 11/2, 190–205).

Compounds of formula II are obtained by various routes. Thus, compounds II (in which $R^1$ denotes an alkyl radical) are conventionally obtained by alkylating the corresponding compound II in which $R^1$ denotes a hydrogen atom. Suitable bases, for example sodium hydride, sodium amide or potassium t.-butanolate, are used to deprotonate the compound II in which $R^1$ denotes a hydrogen atom. The deprotonation is carried out in inert, anhydrous, if appropriate polar, solvents, such as dimethyl sulfoxide or dioxan. The subsequent alkylation, for example using a dialkyl sulfate, such as dimethyl sulfate, or an alkyl halide, such as butyl iodide, yields the desired product II in which $R^1$ represents an alkyl radical.

Products II in which $R^1$ represents an alkyl radical and products II in which $R^1$ represents a hydrogen atom are also obtained by cyclizing compounds of the formula

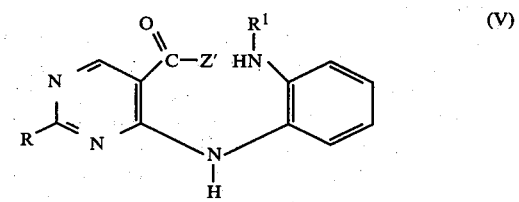

wherein

R and $R^1$ have their previously-ascribed meanings and

Z′ represents a suitable leaving group.

A suitable leaving group Z′ is a group which represents together with the carbonyl group to which it is bound a reactive carboxylic acid derivative.

A suitable leaving group Z′ is, for example, an alkoxy group, or a hydroxy group, or in particular a OH-group which is converted in situ into a chlorine atom by reaction with triphenylphosphine and carbon tetrachloride [see L. C. Barstow et al, J. Org. Chem. 36, 1305 (1971)].

The cyclisation is carried out in a manner which is in itself known and which depends from the nature of the leaving group Z′. If Z′ is an alkoxy group, it is carried out in inert, preferably polar organic solvents, such as lower alcohols, for example ethanol, if appropriate in the presence of an acid, such as a halogen hydracid, or preferably in the presence of a base, for example an alkali metal alkanolate, at temperatures between 50° and 100° C., preferably at the boiling point of the solvent concerned. If Z′ is a hydroxy group, the cyclisation is carried out in inert solvents and preferably in the presence of a condensation agent, such as dicyclohexylcarbodiimide. If Z′ is a OH-group which is converted in situ into a chlorine atom, the cyclisation is carried out in an inert solvent, for example in dioxan or tetrahydrofuran, at temperatures between 50° and 100° C., preferably at the boiling point of the solvent concerned.

Compounds of formula V are prepared in a conventional manner by reacting a pyrimidine VI with an o-phenylenediamine VII

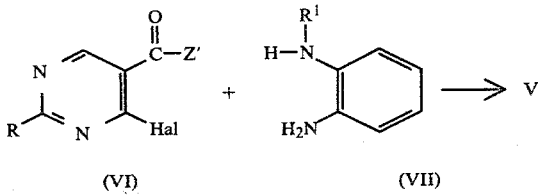

wherein

R, R[1] and Z' have their previously-noted meanings and

Hal represents a halogen atom, in particular a chlorine atom.

The reaction is carried out, for example, in inert, polar organic solvent, such as ethanol, ethyl acetate or preferably dimethyl formamide, with the addition of a proton acceptor, such as triethylamine or sodium carbonate, at the boiling point of the solvent. Compound of formulae VI and VII (used as starting materials) are either known or are readily prepared by known processes from available compounds.

The examples which follow illustrate the invention in greater detail without limiting it. The abbreviation m.p. denotes melting point; dec. denotes decomposition point. "Ether" is to be understood as diethyl ether.

EXAMPLE 1

11-[(4-Methyl-1-piperazinyl)acetyl]-5,6-dihydropyrimido[4,5-b][1,5]benzodiazepin-5-one 2.00 g (0.02 mol) of N-methylpiperazine in 20 ml of absolute benzene are added to a suspension of 2.89 g (0.01 mol) of 11-chloroacetyl-5,6-dihydropyrimido[4,5-b][1,5]benzodiazepin-5-one in 30 ml of absolute benzene, and the obtained mixture is heated for 1 hour under reflux. The solvent is removed on a rotary evaporator, and 70 ml of saturated sodium bicarbonate solution are added to the residue. The mixture is extracted 3 times, each with 100 ml of chloroform, and the organic phase is washed with water, dried and concentrated in vacuo. The residue which remains is chromatographed on neutral silica gel using 8:2 chloroform/methanol as the eluant; yield 1.2 g, with m.p. 203° to 205° C. (dec.).

The following salts are obtained by adding the acids: the dihyrochloride [m.p. 198° to 200° C. (dec.)], the fumarate [m.p. 195° C. (dec.), from isopropanol] and the maleate [m.p. 208° C. (dec.), from isopropanol].

EXAMPLE 2

11-Piperidinoacetyl-5,6-dihydropyrimido[4,5-b][1,5]benzodiazepin-5-one 2 g of the title compound, m.p. 250° to 252° C. (dec.), are obtained analogously to Example 1 from 5.76 g (0.02 mol) of 11-chloroacetyl-5,6-dihydropyrimido[4,5-b][1,5]benzodiazepin-5-one and 3.4 g (0.04 mol) of piperidine.

EXAMPLE 3

11-Dimethylaminoacetyl-5,6-dihydropyrimido[4,5-b][1,5]benzodiazepin-5-one 5.0 g (0.0174 mol) of 11-chloroacetyl-5,6-dihydropyrimido[4,5-b][1,5]benzodiazepin-5-one are added at 10° C. to 150 ml of a saturated solution of dimethylamine in absolute ethanol, the mixture is stirred for a further 15 minutes at the same temperature and the volatile constituents are then removed on a rotary evaporator. 50 ml of saturated sodium bicarbonate solution are added to the residue, the mixture is extracted several times with chloroform and the organic phase is dried and concentrated. The residue is recrystallized from 6:4 ethyl acetate/methylene chloride; yield: 2.2 g, m.p. 208° to 210° C.

EXAMPLE 4

11-(1-Piperazinyl-acetyl)-5,6-dihydropyrimido[4,5-b][1,5]benzodiazepin-5-one 1.2 g of Piperazine are added at room temperature to a solution of 1.0 g of 11-chloroacetyl-5,6-dihydropyrimido[4,5-b][1,5]benzodiazepin-5-one in 10 ml of absolute dioxan, and the obtained mixture is heated for 1 hour at 80° C. The solvent is removed on a rotary evaporator, and 50 ml of saturated sodium bicarbonate solution are added to the residue. The mixture is extracted several times with chloroform, and the organic phase is dried and concentrated. The residue is recrystallized from isopropanol; yield: 0.4 g, m.p. 200° C. (dec.).

EXAMPLE 5

11-[N-(2-dimethylaminoethyl)-N-methylamino]acetyl-5,6-dihydropyrimido[4,5-b][1,5]benzodiazepin-5-one 0.45 g of the title compound are obtained analogously to Example 4 from 2.6 g of N,N,N'-trimethylethylenediamine and 3.0 g of 11-chloroacetyl-5,6-dihydropyrimido[4,5-b][1,5]benzodiazepin-5-one in 20 ml of absolute dioxan. The mixture is stirred for 3 hours at room temperature. Purification is carried out by precipitating the dihydrochloride (m.p. 184° to 186° C.).

EXAMPLE 6

11-[(N-ethyl-n-butylamino)acetyl]-5,6-dihydropyrimido[4,5-b][1,5]benzodiazepin-5-one 2.2 g of the title compound [m.p. 151° to 152° C., from isopropanol] are obtained analogously to Example 4 from 2.6 g of N-ethyl(n-butyl)amine and 3.7 g of 11-chloroacetyl-5,6-dihydropyrimido[4,5-b][1,5]benzodiazepin-5-one in 20 ml of absolute dioxan.

The mixture is stirred for 2 hours at 70° C., concentrated in vacuo, and chromatographed on neutral silica gel using 95:5 methylene chloride/methanol as the eluant.

EXAMPLE 7

11-Morpholinoacetyl-5,6-dihydropyrimido[4,5-b][1,5]benzodiazepin-5-one 2.2 g of the title compound (m.p. 240° to 242° C., from ethanol) are obtained analogously to Example 4 from 2.2 g of morpholine and 3.6 g of 11-chloroacetyl-5,6-dihydropyrimido[4,5-b][1,5]benzodiazepin-5-one in 20 ml of absolute dioxan.

The mixture is stirred for 6 hours at 50° C.

Purification is carried out by precipitating the hydrochloride [m.p. 200° C. (dec.), from isopropanol].

EXAMPLE 8

6-Methyl-11-[(4-methyl-1-piperazinyl)acetyl]-5,6-dihydropyrimido[4,5-b][1,5]benzodiazepin-5-one 2.6 g (0.0266 mol) of N-methylpiperazine are added dropwise at 50° C., in the course of 15 minutes, to a suspension of 4.0 g (0.0133 mol) of 11-chloroacetyl-6-methyl-5,6-dihydropyrimido[4,5-b][1,5]benzodiazepin-5-one in 30 ml of absolute benzene, and the mixture is stirred for a further 1.5 hours at 70° C. After cooling, the mixture is poured into 100 ml of saturated sodium bicarbonate solution and is extracted once with 50 ml of ethyl acetate and twice with 100 ml, each time, of chloroform. After drying, the organic phase is concentrated in vacuo, and the liquid residue is induced to crystallize by means of ether. It is purified by filtering through neutral silica gel (elution with chloroform) and evaporating the filtrate; yield: 2.7 g, m.p. 183° to 185° C.

EXAMPLE 9

6-Methyl-11-piperidinoacetyl-5,6-dihydropyrimido[4,5-b][1,5]benzodiazepin-5-one 1.8 g of the title compound, m.p. 203° to 204° C., are obtained analogously to Example 8 from 2.3 g (0.0076 mol) of 11-chloroacetyl-6-methyl-5,6-dihydropyrimido[4,5-b][1,5]benzodiazepin-5-one in 15 ml of absolute benzene and 1.94 g (0.0228 mol) of piperidine in 5 ml of absolute benzene.

EXAMPLE 10

11-[(N-ethyl-n-butylamino)acetyl]-6-methyl-5,6-dihydropyrimido[4,5-b][1,5]benzodiazepin-5-one 1.5 g of the title compound (m.p. 131° to 133° C., from isopropanol) are obtained analogously to Example 8 from 1.14 g of N-ethyl-(n-butyl)amine and 1.7 g of 11-chloroacetyl-6-methyl-5,6-dihydropyrimido[4,5-b][1,5]benzodiazepin-5-one in 20 ml of absolute benzene by stirring the mixture under reflux for 2.5 hours.

EXAMPLE 11

6-Methyl-11-(1-perhydroazepinylacetyl)-5,6-dihydropyrimido[4,5-b][1,5]benzodiazepin-5-one 0.6 g of the title compound (m.p. 206° to 207° C., from isopropanol) are obtained analogously to Example 8 from 0.34 g of perhydroazepine and 0.5 g of 11-chloroacetyl-6-methyl-5,6-dihydropyrimido[4,5-b][1,5]benzodiazepin-5-one in 20 ml of absolute benzene by stirring the mixture under reflux for 1 hour.

EXAMPLE 12

6-(n-Butyl)-11-[(4-methyl-1-piperazinyl)acetyl]-5,6-dihydropyrimido[4,5-b][1,5]benzodiazepin-5-one 2.0 g of the title compound (m.p. 153° to 154° C., from isopropanol) are obtained analogously to Example 8 from 3.0 g of N-methylpiperazine and 3.5 g of 6-(n-butyl)-11-chloroacetyl-5,6-dihydropyrimido[4,5-b][1,5]benzodiazepin-5-one in 140 ml of absolute toluene by stirring the mixture for 2.5 hours at 80° C.

EXAMPLE 13

6-(n-Butyl)-11-morpholinoacetyl-5,6-dihydropyrimido[4,5-b][1,5]benzodiazepin-5-one 2.0 g of the title compound (m.p. 127° to 128° C., from isopropanol) are obtained analogously to Example 8 from 2.65 g of morpholine and 3.5 g of 6-(n-butyl)-11-chloroacetyl-5,6-dihydropyrimido[4,5-b][1,5]benzodiazepin-5-one in 40 ml of absolute toluene by stirring the mixture for 3.5 hours at 80° C. Purification is carried out by precipitating the hydrochloride [m.p. 195° (dec.), from isopropanol].

EXAMPLE 14

6-Isopropyl-11-[(4-methyl-1-piperazinyl)acetyl]-5,6-dihydropyrimido[4,5-b][1,5]benzodiazepin-5-one 1.7 g of the title compound (m.p. 133° to 135° C., from ethyl acetate/petroleum ether) are obtained analogously to Example 8 from 1.7 g of N-methylpiperazine and 2.8 g of 11-chloroacetyl-6-isopropyl-5,6-dihydropyrimido[4,5-b][1,5]benzodiazepin-5-one in 20 ml of absolute dioxan by stirring the mixture for 1 hour at 80° C.

EXAMPLE 15

11-Diallylaminoacetyl-6-isopropyl-5,6-dihydropyrimido[4,5-b][1,5]benzodiazepin-5-one 2.0 g of the title compound (oil) are obtained analogously to Example 8 from 1.7 g of diallylamine and 2.8 g of 11-chloroacetyl-6-isopropyl-5,6-dihydropyrimido[4,5-b][1,5]benzodiazepin-5-one in 20 ml of absolute dioxan by stirring the mixture for 5 hours at 100° C. Purification is carried out by precipitating the hydrochloride [m.p. 205° C. (dec.)].

EXAMPLE 16

6-Methyl-11-[(4-methyl-1-piperazinyl)acetyl]-2-phenyl-5,6-dihydropyrimido[4,5-b][1,5]benzodiazepin-5-one A mixture of 3.3 g (8.7 mmols) of 11-chloroacetyl-6-methyl-2-phenyl-5,6-dihydropyrimido[4,5-b][1,5]benzodiazepin-5-one, 1.9 ml (17.4 mmols) of N-methylpiperazine and 40 ml of absolute toluene is heated at 70° to 80° C. for 2 hours. After cooling, the reaction mixture is stirred with 40 ml of water. The organic phase is dried with sodium sulfate and evaporated. The yellow crystals remaining are stirred thoroughly with diethyl ether; yield 2.2 g of the title compound, with m.p. 234° to 235° C. (after hot extraction with ethanol).

Dissolution of the product in a half-concentrated hydrochloric acid and evaporation to dryness yield the dihydrochloride of the title compound [m.p. 198° C. (dec.), and methanol].

EXAMPLE 17

6-Methyl-2-phenyl-11-pyrrolidinoacetyl-5,6-dihydropyrimido[4,5-b][1,5]benzodiazepin-5-one 1.35 g (19 mmol) of pyrrolidine are added slowly at 40° C. to a solution of 3 g (7 mmol) of 11-chloroacetyl-6-methyl-2-phenyl-5,6-dihydropyrimido[4,5-b][1,5]benzodiazepin-5-one in 30 ml of absolute toluene, while stirring. The mixture is stirred for a further 6 hours at 60° C. After filtration the solvent is removed on a rotary evaporator, and the residue is purified by chromatography on neutral silica gel using 99:1 chloroform/methanol as the eluant. After removing the solvent, the residue is stirred with methanol and finally recrystallized from ethanol; yield 1.1 g (34%), m.p. 196° C.

EXAMPLE 18

6-Methyl-2-phenyl-11-piperidinoacetyl-5,6-dihydropyrimido[4,5-b][1,5]benzodiazepin-5-one 4.6 g (45%) of the title compound (m.p. 203° to 205° C., from methanol) are obtained analogously to Example 17 from 5.1 g (60 mmol) of piperidine and 9.1 g (24 mmol) of 11-chloroacetyl-6-methyl-2-phenyl-5,6-dihydropyrimido[4,5-b][1,5]benzodiazepin-5-one in 180 ml of absolute toluene by stirring the mixture for 6.5 hours at 110° C.

Dissolution of the product in a half-concentrated hydrochloric acid and evaporation to dryness yields the dihydrochloride of the title compound [m.p. 165° to 168° C. (dec.), from ethanol].

EXAMPLE 19

11-[(N-ethyl-n-butylamino)acetyl]-6-methyl-2-phenyl-5,6-dihydropyrimido[4,5-b][1,5]benzodiazepin-5-one 4.5 g (34%) of the title compound (m.p. 107° to 109° C., from methanol) are obtained analogously to Example 17 from 7.6 g (75 mmol) of N-(n-butyl)-ethylamine and 11.4 g (30 mmol) of 11-chloroacetyl-6-methyl-2-phenyl-5,6-dihydropyrimido[4,5-b][1,5]benzodiazepin-5-one in 200 ml of absolute toluene by stirring the mixture for 7 hours at 110° C.

EXAMPLE 20

11-Diallylaminoacetyl-6-methyl-2-phenyl-5,6-dihydropyrimido[4,5-b][1,5]benzodiazepin-5-one 2.1 g (80%) of the title compound (m.p. 139° to 140° C., from isopropanol) are obtained analogously to Example 17 from 1.46 g (15 mmol) of diallylamine and 2.4 g (6 mmol) of 11-chloroacetyl-6-methyl-2-phenyl-5,6-dihydropyrimido[4,5-b][1,5]benzodiazepin-5-one in 20 ml of absolute toluene by stirring the mixture for 5 hours at 110° C.

EXAMPLE 21

6-Methyl-11-(1-perhydroazepinylacetyl)-2-phenyl-5,6-dihydropyrimido]4,5-b][1,5]benzodiazepin-5-one 9.4 g (73%) of the title compound (m.p. 215° C. to 216° C., from ethanol) are obtained analogously to Example 17 from 7.3 g (73 mmol) of perhydroazepine and 11 g (29 mmol) of 11-chloroacetyl-6-methyl-2-phenyl-5,6-dihydropyrimido[4,5-b][1,5]benzodiazepin-5-one in 200 ml of absolute toluene by stirring the mixture for 7 hours at 110° C.

EXAMPLE 22

6-Methyl-11-morpholinoacetyl-2-phenyl-5,6-dihydropyrimido[4,5-b][1,5]benzodiazepin-5-one 9.6 g (77%) of the title compound (m.p. 180° to 181° C., from ethanol) are obtained analogously to Example 17 from 6.4 g (73 mmol) of morpholine and 11 g (29 mmol) of 11-chloroacetyl-6-methyl-2-phenyl-5,6-dihydropyrimido[4,5-b][1,5]benzodiazepin-5-one in 200 ml of absolute toluene by stirring the mixture for 7 hours at 110° C.

EXAMPLE 23

11-[(4-Benzyl-1-piperazinyl)acetyl]-6-methyl-2-phenyl-5,6-dihydropyrimido[4,5-b][1,5]benzodiazepin-5-one 9.5 g (70%) of the title compound (m.p. 194° C.) are obtained analogously to Example 17 from 13.9 g (79 mmol) of N-benzylpiperazine and 10 g (26 mmol) of 11-chloroacetyl-6-methyl-2-phenyl-5,6-dihydropyrimido[4,5-b][1,5]benzodiazepin-5-one in 200 ml of absolute toluene by stirring the mixture for 7 hours at 110° C.

EXAMPLE 24

11-[{N-(n-butyl)-N-(tert.-butyl)amino}-acetyl]-6-methyl-2-phenyl-5,6-dihydropyrimido[4,5-b][1,5]benzodiazepin-5-one 1 g of the title compound (m.p. 111° to 113° C.) is obtained analogously to Example 17 from 11.6 g (90 mmol) of N-butyl-(tert.-butyl)amino and 11.4 g (30 mmol) of 11-chloroacetyl-6-methyl-2-phenyl-5,6-dihydropyrimido[4,5-b][1,5]benzodiazepin-5-one in 200 ml of absolute toluene by stirring the mixture for 140 hours at 110° C.

EXAMPLE 25

11-[N-(2-dimethylaminoethyl)-N-methylamino]acetyl-6-methyl-2-phenyl-5,6-dihydropyrimido[4,5-b][1,5]benzodiazepin-5-one 0.6 g (25%) of the title compound (m.p. 125° C., from isopropanol) are obtained analogously to Example 17 from 1.43 g (14 mmol) of N,N,N'-trimethyl-ethylendiamine and 2.1 g (5.5 mmol) of 11-chloroacetyl-6-methyl-2-phenyl-5,6-dihydropyrimido[4,5-b][1,5]benzodiazepin-5-one in 40 ml of absolute toluene by stirring the mixture for 4 hours at 110° C.

EXAMPLE 26

11-Dimethylaminoacetyl-6-methyl-2-phenyl-5,6-dihydropyrimido[4,5-b][1,5]benzodiazepin-5-one 2.8 g (48%) of the title compound (m.p. 207° to 208° C., from methanol) are obtained analogously to Example 17 from 11 g (98 mmol) of dimethylamine (in form of a 40 percent aqueous solution) and 5.5 g (15 mmol) of 11-chloroacetyl-6-methyl-2-phenyl-5,6-dihydropyrimido[4,5-b][1,5]benzodiazepin-5-one in 55 ml of dichloromethane by stirring the mixture for 7 hours at 40° C.

EXAMPLE 27

11-Diisopropylaminoacetyl-6-ethyl-2-phenyl-5,6-dihydropyrimido[4,5-b][1,5]benzodiazepin-5-one 5.2 g (50%) of the title compound (m.p. 120° to 121° C., from cyclohexane) are obtained analogously to Example 17 from 10 g (100 mmol) of diisopropylamine and 9 g (23 mmol) of 11-chloroacetyl-6-ethyl-2-phenyl-5,6-dihydropyrimido[4,5-b][1,5]benzodiazepin-5-one in 150 ml of absolute dioxan. A small amount of potassium iodide (as a catalyst) is added to the mixture which is stirred under reflux for 80 hours.

EXAMPLE 28

11-[{N-(n-butyl)-N-(tert.butyl)-amino}-acetyl]-6-ethyl-2-phenyl 5,6-dihydropyrimido[4,5-b][1,5]benzodiazepin-5-one 3.5 g (33%) of the title compound (m.p. 70° to 72° C.) are obtained analogously to Example 17 from 16.6 g (129 mmol) of N-butyl-(tert.-butyl)-amine and 9 g (23 mmol) of 11-chloroacetyl-6-ethyl-2-phenyl-5,6-dihydropyrimido[4,5-b][1,5]benzodiazepin-5-one in 150 ml of absolute dioxan. A small amount of potassium iodide (as a catalyst) is added to the mixture which is stirred under reflux for 58 hours.

EXAMPLE 29

11-[(4-Methyl-1-piperazinyl)acetyl]-2-phenyl-6-(n-propyl)-5,6-dihydropyrimido[4,5-b][1,5]benzodiazepin-5-one 2.3 g (80%) of the title compound (m.p. 148° to 150° C., from isopropanol) are obtained analogously to Example 17 from 1 g (10 mmol) of N-methylpiperazine and 2.5 g (6 mmol) of 11-chloroacetyl-2-phenyl-6-n-propyl-5,6-dihydropyrimido[4,5-b][1,5]benzodiazepin-5-one in 30 ml of absolute dioxan by stirring the mixture for 5 hours at 50° C.

EXAMPLE 30

6-Isopropyl-11-[(4-methyl-1-piperazinyl)acetyl]-2-phenyl-5,6-dihydropyrimido[4,5-b][1,5]benzodiazepin-5-one 11.5 g (80%) of the title compound (m.p. 168° to 170° C., from acetone) are obtained analogously to Example 17 from 10 g (100 mmol) of N-methylpiperazine and 12.5 g (31 mmol) of 11-chloroacetyl-6-isopropyl-2-phenyl-5,6-dihydropyrimido[4,5-b][1,5]benzodiazepin-5-one in 120 ml of absolute dioxan by stirring the mixture under reflux for 6 hours.

EXAMPLE 31

6-Isopropyl-2-phenyl-11-piperidinoacetyl-5,6-dihydropyrimido[4,5-b][1,5]benzodiazepin-5-one 5.85 g (75%) of the title compound (m.p. 152° to 154° C., from isopropanol) are obtained analogously to Example 17 from 3 g (35 mmol) of piperidine and 7 g (17 mmol) of 11-chloroacetyl-6-isopropyl-2-phenyl-5,6-dihydropyrimido-[4,5-b][1,5]benzodiazepin-5-one in 70 ml of absolute dioxan by stirring the mixture under reflux for 16 hours.

EXAMPLE 32

6-Isopropyl-11-(1-perhydroazepinylacetyl)-2-phenyl-5,6-dihydropyrimido[4,5-b][1,5]-benzodiazepin-5-one 3.6 g (63%) of the title compound (m.p. 180° to 182° C., from isopropanol) are obtained analogously to Example 17 from 2.5 g (25 mmol) of perhydroazepine and 5 g (12.5 mmol) of 11-chloroacetyl-6-isopropyl-2-phenyl-5,6-dihydropyrimido[4,5-b][1,5]benzodiazepin-5-one in 50 ml of absolute toluene by stirring the mixture under reflux for 3 hours.

EXAMPLE 33

6-(n-Butyl)-11-[(4-methyl-1-piperazinyl)acetyl]-2-phenyl-5,6-dihydropyrimido[4,5-b][1,5]benzodiazepin-5-one 4.4 g (38%) of the title compound (m.p. 90° to 94° C., from acetone) are obtained analogously to Example 17 from 10 g (100 mmol) of N-methylpiperazine and 10 g (24 mmol) of 6-(n-butyl)-11-chloroacetyl-2-phenyl-5,6-dihydropyrimido[4,5-b][1,5]benzodiazepin-5-one in 100 ml of absolute dioxan by stirring the mixture under reflux for 4 hours.

EXAMPLE 34

6-(n-Butyl)-11-diallylaminoacetyl-2-phenyl-5,6-dihydropyrimido[4,5-b][1,5]benzodiazepin-5-one 6.7 g (73%) of the title compound (m.p. 137° to 138° C., from cyclohexane) are obtained analogously to Example 17 from 9.7 g (100 mmol) of diallylamine and 8 g (19 mmol) of 6-(n-butyl)-11-chloroacetyl-2-phenyl-5,6-dihydropyrimido[4,5-b][1,5]benzodiazepin-5-one in 150 ml of absolute dioxan by stirring the mixture under reflux for 5 hours.

EXAMPLE 35

6-(n-Butyl)-11-di-n-butylaminoacetyl-2-phenyl-5,6-dihydropyrimido[4,5-b][1,5]benzodiazepin-5-one 6.6 g (68%) of the title compound (m.p. 103° to 104° C., from cyclohexane) are obtained analogously to Example 17 from 12.9 g (100 mmol) of di-(n-butyl)amine and 8 g (19 mmol) of 6-(n-butyl)-11-chloroacetyl-2-phenyl-5,6-dihydropyrimido[4,5-b][1,5]benzodiazepin-5-one in 150 ml of absolute dioxan by stirring the mixture under reflux for 4 hours.

The fumarate of the title compound melts at 114° to 115° C. (from isopropanol).

EXAMPLE 36

6-(sec.-Butyl)-11-[(4-methyl-1-piperazinyl)acetyl]-2-phenyl-5,6-dihydropyrimido[4,5-b][1,5]benzodiazepin-5-one 2.6 g (53%) of the title compound (m.p. 153° C. to 154° C., from isopropanol) are obtained analogously to Example 17 from 5 g (50 mmol) of N-methylpiperazine and 4.3 g (10 mmol) of 6-(sec.-butyl)-11-chloroacetyl-2-phenyl-5,6-dihydropyrimido[4,5-b][1,5]benzodiazepin-5-one in 40 ml of absolute dioxan by stirring the mixture under reflux for 5 hours.

EXAMPLE 37

11-(1-Homopiperazinyl-acetyl)-6-isobutyl-2-phenyl-5,6-dihydropyrimido[4,5-b][1,5]benzodiazepin-5-one 0.4 g of the title compound (m.p. 118° to 120° C., from isopropanol) are obtained analogously to Example 17 from 1.3 g (13 mmol) of homopiperazine, 1.3 g (13 mmol) of triethylamine and 5.5 g (13 mmol) of 11-chloroacetyl-6-isobutyl-2-phenyl-5,6-dihydropyrimido[4,5-b][1,5]benzodiazepin-5-one in 50 ml of absolute dioxan by stirring the mixture for 6 hours at 50° C.

EXAMPLE 38

6-Isobutyl-11-piperidinoacetyl-2-phenyl-5,6-dihydropyrimido[4,5-b][1,5]benzodiazepin-5-one 3.5 g (45%) of the title compound (m.p. 193° to 194° C., from isopropanol) are obtained analogously to Example 17 from 8.5 g (100 mmol) of piperidine and 7 g (16.6 mmol) of 11-chloroacetyl-6-isobutyl-2-phenyl-5,6-dihydropyrimido[4,5-b][1,5]benzodiazepin-5-one in 70 ml of absolute dioxan by stirring the mixture under reflux for 3 hours.

EXAMPLE 39

6-(tert.-Butyl)-11-piperidinoacetyl-2-phenyl-5,6-dihydropyrimido[4,5-b][1,5]benzodiazepin-5-one 1.8 g (26%) of the title compound (m.p. 193° to 194° C., from isopropanol) are obtained analogously to Example 17 from 8.5 g (100 mmol) of piperidine and 6.3 g (15 mmol) of 6-(tert.-butyl)-11-chloroacetyl-2-phenyl-5,6-dihydropyrimido[4,5-b][1,5]benzodiazepin-5-one in 70 ml of absolute dioxan by stirring the mixture under reflux for 3 hours.

EXAMPLE 40

6-Methyl-2-phenyl-11-[2-(piperidino)propionyl]-5,6-dihydropyrimido[4,5-b][1,5]benzodiazepin-5-one 2 g (45%) of the title compound (m.p. 214° to 215° C., from ethanol) are obtained analogously to Example 17 from 1.7 g (20 mmol) of piperidine and 4.5 g (10 mmol) of 11-[2-(bromopropionyl)-6-methyl-2-phenyl-5,6-dihydropyrimido[4,5-b][1,5]benzodiazepin-5-one in 90 ml of absolute toluene by stirring the mixture for 4 hours at 110° C.

EXAMPLE 41

6-Methyl-2-phenyl-11-[2-(piperazino)propionyl]-5,6-dihydropyrimido[4,5-b][1,5]benzodiazepin-5-one 0.3 g of the title compound (m.p. 197° C., from isopropanol) is obtained analogously to Example 17 from 1.76 g (20 mmol) of piperazine and 4.5 g (10 mmol) of 11-[2-(bromopropionyl)]-6-methyl-2-phenyl-5,6-dihydropyrimido[4,5-b][1,5]benzodiazepin-5-one in 90 ml of absolute toluene by stirring the mixture for 10 hours at 110° C.

EXAMPLE 42

6-Methyl-11-[(4-methyl-1-piperazinyl)acetyl]-2-phenyl-5,6-dihydropyrimido[4,5-b][1,5]benzodiazepin-5-one-N-oxide A solution of 0.7 g (3.4 mmol) of m-chloroperbenzoic acid (85 percent) in 10 ml of methanol is slowly added at room temperature to a suspension of 1 g (2,3 mmol) of 6-methyl-11-[(4-methyl-1-piperazinyl)acetyl]-2-phenyl-5,6-dihydropyrimido[4,5-b][1,5]benzodiazepin-5-one in 40 ml of methanol. After stirring for 3 hours at 20° C. and filtering, the filtrate is concentrated in vacuo and the residue is purified by chromatography on neutral silica gel using 20:1 chloroform/methanol as the eluant. Yield: 0.5 g (48%).

EXAMPLE 43

11-Chloroacetyl-5,6-dihydropyrimido[4,5-b][1,5]benzodiazepin-5-one

A solution of 3.16 g (0.028 mol) of chloroacetyl chloride in 8 ml of absolute dioxan and a solution of 2.82 g (0.028 mol) of dry triethylamine in 6 ml of absolute dioxan are added dropwise, simultaneously and as uniformly as possible, in the course of 20 minutes, at 60° to 70° C., to a suspension of 4.24 g (0.02 mol) of 5,6-dihydropyrimido[4,5-b][1,5]benzodiazepin-5-one in 60 ml of absolute dioxan, while stirring. The mixture is heated under reflux for a further 4 hours; precipitated triethylamine hydrochloride is filtered off, and the filtrate is concentrated in vacuo. The residue is chromatographed on neutral silica gel, using chloroform; the eluate is evaporated and the residue therefrom is stirred with ether and, after filtration, recrystallized from ethanol; yield: 3.9 g, m.p. 196° C. (dec.), from isopropanol.

EXAMPLE 44

11-Chloroacetyl-6-methyl-5,6-dihydropyrimido[4,5-b][1,5]benzodiazepin-5-one 6.25 g (0.044 mol) of chloroacetyl chloride in 15 ml of absolute dioxan and 4.4 ml of dry pyridine in 15 ml of dioxan are added dropwise simultaneously (at 80° C. and in the course of 20 minutes) to a suspension of 4.6 g (0.020 mol) of 6-methyl-5,6-dihydropyrimido[4,5-b][1,5]benzodiazepin-5-one in 35 ml of absolute dioxan. The mixture is heated at the boil for a further 15 minutes and is then allowed to cool. The supernatant liquid is decanted off from the heavy dark phase, and the latter is washed with methylene chloride; the dioxan and methylene chloride phases are concentrated in vacuo. The oil which remains is dissolved in a little chloroform and filtered through neutral silica gel; the filtrate is evaporated and the residue is recrystallized from isopropanol, yield: 2.8 g, m.p. 176° to 178° C. (dec.).

EXAMPLE 45

6-(n-Butyl)-11-chloroacetyl-5,6-dihydropyrimido[4,5-b][1,5]benzodiazepin-5-one

The title compound (oil) is obtained analogously to Example 44 from chloroacetyl chloride and 6-(n-butyl)-5,6-dihydropyrimido[4,5-b][1,5]benzodiazepin-5-one in absolute dioxan by stirring the mixture under reflux for 2 hours and using triethylamine instead of pyridine.

EXAMPLE 46

11-Chloroacetyl-6-isopropyl-5,6-dihydropyrimido[4,5-b][1,5]benzodiazepin-5-one

The title compound (oil) is obtained analogously to Example 44 from chloroacetyl chloride and 6-isopropyl-5,6-dihydropyrimido[4,5-b][1,5]benzodiazepin-5-one in absolute dioxan by stirring the mixture under reflux for 2 hours and using triethylamine instead of pyridine.

EXAMPLE 47

11-Chloroacetyl-6-methyl-2-phenyl-5,6-dihydropyrimido[4,5-b][1,5]benzodiazepin-5-one 1.6 ml (20 mmols) of chloroacetyl chloride are added dropwise at room temperature to a suspension of 3 g (10 mmols) of 6-methyl-2-phenyl-5,6-dihydropyrimido[4,5-b][1,5]benzodiazepin-5-one in 30 ml of absolute toluene, and the mixture is then heated under reflux for 3 hours. After cooling, the precipitate which has been deposited is filtered off, and the filtrate is evaporated. The residue is stirred thoroughly with diethyl ether; yield: 3.3 g (86%) with m.p. 189° to 190° C. (from 2-butanone).

EXAMPLE 48

11-Chloroacetyl-6-ethyl-2-phenyl-5,6-dihydropyrimido[4,5-b][1,5]benzodiazepin-5-one 28 g (250 mmol) of chloroacetyl chloride and 28 g (250 mmol) of sodium carbonate are added to a solution of 20 g (63 mmol) of 6-ethyl-2-phenyl-5,6-dihydropyrimido[4,5-b][1,5]benzodiazepin-5-one in 500 ml of absolute toluene. The mixture is stirred for 20 hours at 100° C. The solvent is removed on a rotary evaporator, and the residue is neutralized with 2 N-hydrochloric acid. The mixture is extracted with chloroform, and the organic phase is washed with water, dried and concentrated in vacuo. The residue which remains is recrystallized from isopropanol; yield: 19.2 g (77%), m.p. 147° to 148° C.

EXAMPLE 49

11-Chloroacetyl-2-phenyl-6-(n-propyl)-5,6-dihydropyrimido[4,5-b][1,5]benzodiazepin-5-one 3.2 g (45%) of the title compound (m.p. 139° to 140° C., from isopropanol) are obtained analogously to Example 48 from 5.8 g (17.6 mmol) of 2-phenyl-6-(n-propyl)-5,6-dihydropyrimido[4,5-b][1,5]benzodiazepin-5-one and 5.7 g (50 mmol) of chloroacetyl chloride. Reaction time—65 hours.

EXAMPLE 50

11-Chloroacetyl-6-isopropyl-2-phenyl-5,6-dihydropyrimido[4,5-b][1,5]benzodiazepin-5-one 13.5 g (76%) of the title compound (m.p. 204° to 205° C., from isopropanol) are obtained analogously to Example 48 from 15 g (45 mmol) of 6-isopropyl-2-phenyl- 5,6-dihydropyrimido[4,5-b][1,5]benzodiazepin-5-one and 23 g (200 mmol) of chloroacetyl chloride. Reaction time—60 hours.

EXAMPLE 51

6-(n-Butyl)-11-chloroacetyl-2-phenyl-5,6-dihydropyrimido[4,5-b][1,5]benzodiazepin-5-one 16.1 g (94%) of the title compound (m.p. 139° to 140° C., from isopropanol) are obtained analogously to Example 48 from 14 g (41 mmol) of 6-(n-butyl)-2-phenyl-5,6-dihydropyrimido[4,5-b][1,5]benzodiazepin-5-one and 15 g (130 mmol) of chloroacetyl chloride. Reaction time—24 hours.

EXAMPLE 52

11-Chloroacetyl-6-isobutyl-2-phenyl-5,6-dihydropyrimido[4,5-b][1,5]benzodiazepin-5-one 15.3 g (89%) of the title compound (m.p. 95° to 96° C., from isopropanol) are obtained analogously to Example 48 from 14 g (41 mmol) of 6-isobutyl-2-phenyl-5,6-dihydropyrimido[4,5-b][1,5]benzodiazepin-5-one and 15 g (130 mmol) of chloroacetyl chloride. Reaction time—26 hours.

EXAMPLE 53

6-(sec.-Butyl)-11-chloroacetyl-2-phenyl-5,6-dihydropyrimido[4,5-b][1,5]benzodiazepin-5-one 3.8 g (80%) of the title compound (m.p. 170° to 171° C., from isopropanol) are obtained analogously to Example 48 from 3.9 g (11.3 mmol) of 6-(sec.-butyl)-2-phenyl-5,6-dihydropyrimido[4,5-b][1,5]benzodiazepin-5-one and 3.4 g (30 mmol) of chloroacetyl chloride. Reaction time—15 hours.

EXAMPLE 54

6-(tert.-Butyl)-11-chloroacetyl-2-phenyl-5,6-dihydropyrimido[4,5-b][1,5]benzodiazepin-5-one 13 g (75%) of the title compound (m.p. 176° to 177° C., from isopropanol) are obtained analogously to Example 48 from 14 g (41 mmol) of 6-(tert.-butyl)-2-phenyl-5,6-dihydropyrimido[4,5-b][1,5]benzodiazepin-5-one and 17 g (150 mmol) of chloroacetyl chloride. Reaction time—12 hours.

EXAMPLE 55

11-(2-Bromopropionyl)-6-methyl-2-phenyl-5,6-dihydropyrimido[4,5-b][1,5]benzodiazepin-5-one 6.8 g (23 mmol) of
6-methyl-2-phenyl-5,6-dihydropyrimido[4,5-b][1,5]benzodiazepin-5-one and 7.9 g (46 mmol) of
2-bromopropionyl chloride in 70 ml of absolute toluene are heated for 68 hours under reflux. The slight precipitate which has formed is filtered off, and the solvent is removed on a rotary evaporator. Inoculation and thorough stirring of the remaining tough oil with acetone yields 8.3 of the beige title compound, m.p. 215° C. (from 2-butanone).

EXAMPLE 56

6-Methyl-5,6-dihydropyrimido[4,5-b][1,5]benzodiazepin-5-one (a) 34.4 g (0.125 mol) of 5-ethoxycarbonyl-4-(2-methylaminoanilino)pyrimidine are introduced into a boiling solution of 2.9 g (0.125 mol) of sodium in 150 ml of absolute ethanol, and the mixture is stirred under reflux for 1 hour. After cooling, 9.3 ml of glacial acetic acid are added, and the precipitate is filtered off, washed with ethanol and dried in vacuo; yield 27.5 g, m.p. 236° to 237° C. (from ethanol).

(b) 1 g (0.005 mol) of 5,6-dihydropyirimido[4,5-b][1,5]benzodiazepin-5-one (J. Chem. Soc. C 1968, 1,753) are introduced at room temperature into a solution of 0.617 g (0.0055 mol) of potassium t.-butanolate in 5 ml of absolute dimethyl sulfoxide, while stirring. The mixture is warmed at 50° C. for 15 minutes and is then stirred without heating for a further hour, and 0.915 g (0.0065 mol) of methyl iodide is added. Stirring is continued for 1 hour at room temperature (20° C.) and for 2 hours at 55° C.; after standing overnight, the mixture is introduced into 50 ml of ice water. The mixture is extracted with chloroform, and the organic phase is dried and concentrated. Chromatography on neutral silica gel, using chloroform as the eluant, gives 0.4 g of the title compound, m.p. 236° to 237° C. (from ethanol).

EXAMPLE 57

6-(n-Butyl)-5,6-dihydropyrimido[4,5-b][1,5]benzodiazepin-5-one

The title compound (m.p. 145° to 147° C., from ethanol) is obtained analogously to Example 56a from 5-ethoxycarbonyl-4-[2-(n-butyl)aminoanilino]pyrimidine.

EXAMPLE 58

6-isopropyl-5,6-dihydropyrimido[4,5-b][1,5]benzodiazepin-5-one 12.7 g (0.03 mol) of 5-ethoxycarbonyl-4-(2-isopropylaminoanilino)pyrimidine in 42.2 ml of a 0.1 N. aqueous sodium hydroxide solution are heated for 1 hour under reflux. The solvent is removed on a rotary evaporator and the crystalline residue is dried in vacuo at 60° C. 28.9 g (0.11 mol) of triphenylphosphine and 16.9 g (0.11 mol) of carbon tetrachloride are added to the dry product, dissolved in 150 ml of absolute dioxan, and the mixture is stirred for 5 hours at 80° C. The solvent is removed on a rotary evaporator, and the oily residue which remains is chromatographed on neutral silica gel using 99:1 methylene chloride/methanol as the eluant; yield: 6.3 g, with m.p. 204° to 206° C. (from isopropanol).

EXAMPLE 59

6-Methyl-2-phenyl-5,6-dihydropyrimido[4,5-b][1,5]benzodiazepin-5-one 34.8 g (0.1 mol) of 5-ethoxycarbonyl-4-(2-methylaminoanilino)-2-phenylpyrimidine are added to a freshly prepared, hot solution of 6.8 g (0.296 mol) of sodium in 99 ml of absolute ethanol, while stirring. The orange-colored suspension which has been formed thereby is heated for a further 30 minutes under reflux and is allowed to cool; 19.7 ml of glacial acetic acid and 19.4 ml of water are added and the mixture is stirred for a further 30 minutes. The yellow precipitate is filtered off, washed with water and dried in vacuo; yield: 26 g, with m.p. 227° C. (from ethanol).

EXAMPLE 60

6-Ethyl-2-phenyl-5,6-dihydropyrimido[4,5-b][1,5]benzodiazepin-5-one 21 g (77%) of the title compound (m.p. 198° to 199° C., from isopropanol) are obtained analogously to Example 59 from 31 g (86 mmol) of 5-ethoxycarbonyl-4-(2-ethylaminoanilino)-2-phenylpyrimidine.

EXAMPLE 61

2-Phenyl-6-(n-propyl)-5,6-dihydropyrimido[4,5-b][1,5]benzodiazepin-5-one (a) 7.9 g (30 mmol) of finely powdered triphenylphosphine and 4.6 g (30 mmol) of carbon tetrachloride are added to a solution of 6.2 g (18 mmol) of 4-[2-(n-propyl)aminoanilino]-2-phenyl-5-pyrimidinecarboxylic acid in 40 ml of absolute tetrahydrofurane. The mixture is stirred under reflux for 15 hours. 100 ml of water are added, and the mixture is extracted with chloroform. The organic phase is washed with water, dried and concentrated in vacuo. Yield: 2.5 g (85%), with m.p. 152° to 153° C.

(b) 2 g (22%) of the title compound are obtained analogously to Example 59 from 10.5 g (28 mmol) of 5-ethoxycarbonyl-4-(2-propylaminoanilino)-2-phenylpyrimidine.

EXAMPLE 62

6-Isopropyl-2-phenyl-5,6-dihydropyrimido[4,5-b][1,5]benzodiazepin-5-one (a) 13.5 g (75%) of the title compound (m.p. 195° to 196° C.) are obtained analogously to Example 61a from 19 g (55 mmol) of 4-(2-isopropylaminoanilino)-2-phenyl-5-pyrimidinecarboxylic acid, 29.2 g (111 mmol) of triphenylphosphine and 18.6 g (121 mmol) of carbon tetrachloride.

(b) The title compound is obtained analogously to Example 59 from 5-ethoxycarbonyl-4-(2-isopropylaminoanilino)-2-phenylpyrimidine.

EXAMPLE 63

6-(n-Butyl)-2-phenyl-5,6-dihydropyrimido[4,5-b][1,5]benzodiazepin-5-one 7.5 g (72%) of the title compound (m.p. 140° to 141° C., from isopropanol) are obtained analogously to Example 59 from 22 g (56 mmol) of 5-ethoxycarbonyl-4-[2-(n-butyl)aminoanilino]-2-phenylpyrimidine.

EXAMPLE 64

6-Isobutyl-2-phenyl-5,6-dihydropyrimido[4,5-b][1,5]-benzodiazepin-5-one 15 g (79%) of the title compound (m.p. 203° to 204° C., from isopropanol) are obtained analogously to Example 61a from 20 g (55 mmol) of 4-(2-isobutylaminoanilino)-2-phenyl-5-pyrimidinecarboxylic acid, 26.2 g (100 mmol) of triphenylphosphine and 15.4 g (100 mmol) of carbon tetrachloride.

EXAMPLE 65

6-(sec.-Butyl)-2-phenyl-5,6-dihydropyrimido[4,5-b][1,5]benzodiazepin-5-one 6.2 g (73%) of the title compound (m.p. 203° to 205° C., from isopropanol) are obtained analogously to Example 61a from 9 g (25 mmol) of 4-[2-sec.-butyl)aminoanilino]-2-phenyl-5-pyrimidinecarboxylic acid, 11.5 g (43.8 mmol) of triphenylphosphine and 6.2 g (40 mmol) of carbon tetrachloride.

EXAMPLE 66

6-(tert.-Butyl)-2-phenyl-5,6-dihydropyrimido[4,5-b][1,5]benzodiazepin-5-one

The title compound (m.p. 221° to 222° C., from isopropanol) is obtained analogously to Example 61a from 4-[2-(tert.-butyl)aminoanilino]-2-phenyl-5-pyrimidinecarboxylic acid.

EXAMPLE 67

5-Ethoxycarbonyl-4-(2-methylaminoanilino)pyrimidine 40.4 g (0.4 mol) of triethylamine are first added dropwise, while stirring, to a boiling solution of 48.8 g (0.4 mol) of N-methyl-(o-phenylene)diamine in 500 ml of absolute ethyl acetate, and this dropwise addition is then followed by a solution of 74.4 g (0.4 mol) of 4-chloro-5-ethoxycarbonylpyrimidine in 500 ml of absolute ethyl acetate. The mixture is then heated under reflux for a further 4 hours; the precipitated triethylamine hydrochloride is filtered off while hot, and the filtrate is concentrated. The residue is recrystallized from isopropanol; yield: 34.4 g, m.p. 153° to 155° C.

5-Ethoxycarbonyl-4-[2-(n-butyl)aminoanilino]pyrimidine (m.p. 103° to 104° C., from isopropanol) and 5-ethoxycarbonyl-4-(2-isopropylaminoanilino)pyrimidine (m.p. 103° to 104° C. from isopropanol).

are obtained analogously by reacting
N-(n-butyl)-(o-phenylene)diamine and
N-isopropyl-(o-phenylene)diamine with
4-chloro-5-ethoxycarbonylpyrimidine.

EXAMPLE 68

4-[2-(n-Propyl)aminoanilino]-2-phenyl-5-pyrimidinecarboxylic acid 14.5 g (39 mmol) of 5-ethoxycarbonyl-4-[2-(n-propyl)aminoanilino]-2-:phenylpyrimide and 8.7 g (156 mmol) of potassium hydroxide, dissolved in 140 ml of ethanol and 60 ml of water, are heated under reflux for 5 hours. The solvent is removed on a rotary evaporator. The residue which remains behind is acidified with dilute hydrochloric acid. The mixture is extracted with chloroform. The organic phase is washed with water, dried and concentrated in vacuo. Yield: 5.8 g (46%), with m.p. 205° to 206° C. (from isopropanol).

4-(2-Isopropylaminoanilino)-2-phenyl-5-pyrimidinecarboxylic acid [m.p. 223° to 225° C. (dec.), from isopropanol], 4-(2-isobutylaminoanilino)-2-phenyl-5-pyrimidinecarboxylic acid (m.p. 192° to 193° C.), 4-[2-(sec.-butyl)aminoanilino]-2-phenyl-5-pyrimidinecarboxylic acid (m.p. 202° to 203° C., from isopropanol) and 4-[2-(tert.-butyl)aminoanilino]-2-phenyl-5-pyrimidinecarboxylic acid [monohydrate, m.p. 247° to 248° C. (dec.), from isopropanol]

are obtained analogously from the corresponding ethyl ester.

EXAMPLE 69

5-Ethoxycarbonyl-4-(2-methylaminoanilino)-2-phenylpyrimidine 46.2 g (0.176 mol) of 4-chloro-5-ethoxycarbonyl-2-phenylpyrimidine are added in small portions at 60° C. to a solution of 21.5 g (0.175 mol) of N-methyl-(o-phenylene)diamine and 27 ml (0.19 mol) of triethylamine in 220 ml of absolute ethanol, and the mixture is then heated for a further hour under reflux. After cooling, the yellow precipitate which has been deposited is filtered off, washed with a total of 100 ml of ethanol and dried; yield: 39.4 g (64%), with m.p. 165° C. (from ethyl acetate).

Analogous reactions in toluene (6 hours under reflux), ethyl acetate (6 hours under reflux) and dimethyl formamide (8 hours under reflux) yield 70%, 70% and 90% of the title compound.

5-Ethoxycarbonyl-4-(2-ethylaminoanilino)-2-phenylpyrimidine (m.p. 135° to 136° C.),
5-ethoxycarbonyl-4-[2-(n-propyl)aminoanilino]-2-phenylpyrimidine (m.p. 104° to 105° C.),
5-ethoxycarbonyl-4-(2-isopropylaminoanilino)-2-phenylpyrimidine (m.p. 126° to 127° C.),
5-ethoxycarbonyl-4-[2-(n-butyl)aminoanilino]-2-phenylpyrimidine (m.p. 112° to 113° C.),
5-ethoxycarbonyl-4-(2-isobutylaminoanilino)-2-phenylpyrimidine (m.p. 113° to 115° C.),
5-ethoxycarbonyl-4-[2-(sec.-butyl)aminoanilino]2-phenylpyrimidine (m.p. 94° to 95° C.) and
5-ethoxycarbonyl-4-[2-(tert.-butyl)aminoanilino]-2-phenylpyrimidine (m.p. 127° to 128° C.
are obtained analogously by reacting
N-ethyl-(o-phenylene)diamine,
N-(n-propyl)-(o-phenylene)diamine,
N-isopropyl-(o-phenylene)diamine,
N-(n-butyl)-(o-phenylene)diamine,
N-isobutyl-(o-phenylene)diamine,
N-(sec.-butyl)-(o-phenylene)diamine and
N-(tert.-butyl)-(o-phenylene)diamine with
4-chloro-5-ethoxycarbonyl-2-phenylpyrimidine.

EXAMPLE 70

11-[(4-methyl-1-piperazinyl)acetyl]-2-phenyl-5,6-dihydropyrimido[4,5-b][1,5]benzodiazepin-5-one 0.2 g (52%) of the title compound are obtained anaogously to Example 17 from 0.35 g (0.96 mmol) of 11-chloroacetyl-2-phenyl-5,6-dihydropyrimido[4,5-b][1,5-benzodiazepin-5-one and 0.27 g (2.7 mmol) of N-methylpiperazine in 3.5 ml of absolute dioxan by stirring the mixture under reflux for 5 hours. The crude product is chromatographed on neutral silica gel using methylene chloride as the eluant.

EXAMPLE 71

11-Piperidinoacetyl-2-phenyl-5,6-dihydropyrimido[4,59-b][1,5]benzodiazepin-5-one 0.58 g (47%) of the title compound are obtained analogously to Example 17 from 1.1 g (3 mmol) of 11-chloroacetyl-2-phenyl-5,6-dihydropyrimido[4,5-b][1,5]benzodiazepin-5-one and 0.64 g (7.5 mmol) of piperidine in 10 ml of absolute dioxan by stirring the mixture under reflux for 4 hours. The crude product is chromatographed on neutral silica gel using methylene chloride as the eluant.

EXAMPLE 72

11-Chloroacetyl-2-phenyl-5,6-dihydroxyprimido[4,5-b][1,5]benzodiazepin-5-one 3.3 g (60%) of the title compound (m.p. 228° C. to 232° C.) are obtained analogously to Example 47 from 5 g (15 mmol) of 2-phenyl-5,6-dihydropyrimido[4,5-b][1,5]benzodiazepin-5-one and 6.8 g (60 mmol) of chloroacetyl chloride in 75 ml of toluene by stirring the mixture under reflux for 7 hours.

EXAMPLE 73

2-Phenyl-5,6-dihydropyrimido[4,5-b][1,5]benzodiazepin-5-one 78 g of 5-ethoxycarbonyl-4-(2-aminoanilino)-2-phenylpyrimidine are added to a freshly prepared boiling solution of 8 g (350 mmol) of sodium in 250 ml of absolute ethanol, while stirring. The suspension which has been formed thereby is heated under reflux for about 45 minutes until complete solution is effected. After cooling, the mixture is neutralized with 20 ml (350 mmol) of glacial acetic acid. 200 ml of ethanol and 200 ml of water are added, the precipitate is filtered off, washed with water and dried in vacuo; yield: 66 g (97%), with m.p. 260° to 261° C. (from dimethyl formamide/water).

EXAMPLE 74

5-Ethoxycarbonyl-4-(2-aminoanilino)-2-phenylpyrimidine 49 g (90%) of the title compound (m.p. 154° to 156° C., from ethyl acetate) are obtained analogously to Example 69 from 24 g (220 mmol) of o-phenylenediamine, 42.7 g (163 mmol) of 4-chloro-5-ethoxycarbonyl-2-phenylpyrimidine and 23 g (230 mmol) of triethylamine in 420 ml of absolute ethanol by stirring the mixture under reflux for 1.5 hours.

EXAMPLE 75

11-[N-(2-Dimethylaminoethyl)-N-methylamino]acetyl-2-phenyl-5,6-dihydropyrimido[4,5-b][1,5]benzodiazepin-5-one The title compound is obtained analgously to Example 17 from N,N,N'-trimethyl-ethylenediamine and 11-chloroacetyl-2-phenyl-5,6-dihydropyrimido[4,5-b][1,5]benodiazepin-5-one.

EXAMPLE 76

11-[N-(2-Dimethylaminoethyl)-N-ethylamino]acetyl-2-phenyl-5,6-dihydropyrimido[4,5-b][1,5]benzodiazepin-5-one The title compound is obtained analogously to Example 17 from N-ethyl-N',N'-dimethyl-ethylendiamine and 11-chloroacetyl-2-phenyl-5,6-dihydropyrimido[4,5-b][1,5]benzodiazepin-5-one.

EXAMPLE 77

11-[N-(2-Diethylaminoethyl)-N-ethylamino]acetyl-2-phenyl5,6-dihydropyrimido[4,5-b][1,5]benzodiazepin-5-one The title compound is obtained analogously to Example 17 from N,N,N'-triethyl-ethylendiamine and 11-chloroacetyl-2-phenyl-5,6-dihydropyrimido[4,5-b][1,5]benzodiazepin-5-one.

EXAMPLE 78

11-[N-(2-Dimethylaminoethyl)-N-ethylamino]acetyl-6-methyl-2-phenyl-5,6-dihydropyrimido[4,5-b][1,5]benzodiazepin-5-one The title compound is obtained analogously to Example 17 from N-ethyl-N',N'-dimethyl-ethylendiamine and 11-chloroacetyl-6-methyl-2-phenyl-5,6-dihydropyridmido[4,5-b][1,5]benzodiazepin-5-one.

EXAMPLE 79

11-[N-(2-Diethylaminoethyl)-N-ethylamino]acetyl-6-methyl-2-phenyl-5,6-dihydropyrimido[4,5-b][1,5]benzodiazepin-5-one The title compound is obtained analogously to Example 17 from N,N,N'-triethyl-ethylendiamine and 11- chloroacetyl-6-methyl-2-phenyl-5,6-dihydropyrimido[4,5-b][1,5]benzodiazepin-5-one.

EXAMPLE 80

Tablets containing 20 mg of active compound 10 kg of 6-methyl-2-phenyl-11-piperidinoacetyl-5,6-dihydropyrimido[4,5-b][1,5]benzodiazepin-5-one, 45 kg of lactose, 31 kg of maize starch and 3 kg of polyvinylpyrrolidone are moistened with approx. 20 liters of water and granulated through a sieve with a mesh width of 1.25 mm. The granules are dried in a fluidized bed drier until a relative humidity of from 50 to 60% is reached; 8 kg of sodium carboxymethylcellulose, 2 kg of talc and 1 kg of magnesium stearate are then added. The finished granules are compressed to give tablets weighing 200 mg and having a diameter of 8 mm.

EXAMPLE 81

Capsules containing 15 mg of active compound 150 g of 6-methyl-2-phenyl-11-piperidinoacetyl-5,6-dihydropyrimido[4,5-b][1,5]benzodiazepin-5-one, 845 g of microcrystalline cellulose and 5 g of amorphous silica are finely powdered, mixed thoroughly and filled into hard gelatin capsules of size 4.

EXAMPLE 82

100,000 capsules, each containing 30 mg of active compound, are prepared from the following ingredients:

1,500 g of 6-methyl-2-phenyl-11-piperidinoacetyl-5,6-dihydropyrimido[4,5-b][1,5]benzodiazepin-5-one and 1,500 g of magnesium trisilicate are mixed with 5,000 g of neutral oil (Miglyol ® 812), and the mixture is filled into soft gelatin capsules.

Pharmacology

The excellent protective action on the stomach of the pharmacologically-active benzodiazepinones is demonstrated by a test using so-called Shay rats as a model. The test establishes that the compounds according to the invention are clearly superior to the known commercial product, carbenoxolone, with regard to protective action on the stomach.

The substances investigated in this test are characterized in the table which follows by means of serial numbers which are allocated as follows:

TABLE I

| Serial No. | Name of compound |
|---|---|
| 1 | Carbenoxolone |
| 2 | 11-[(4-methyl-1-piperazinyl)acetyl]-5,6-dihydropyrimido[4,5-b][1,5]benzodiazepin-5-one |
| 3 | 6-methyl-11-[(4-methyl-1-piperazinyl)acetyl]-2-phenyl-5,6-dihydropyrimido[4,5-b][1,5]benzodiazepin-5-one |
| 4 | 6-methyl-2-phenyl-11-piperidoactyl-5,6-dihydropyrimido[4,5-b][1,5]benzodiazepin-5-one |
| 5 | 11-[N-(2-dimethylaminoethyl)-N-methylamino]-acetyl-6-methyl-2-phenyl-5,6-dihydropyrimido[4,5-b][1,5]-benzodiazepin-5-one |

The effect of the compounds according to the invention on the formation, in rats, of gastric ulcers provoked by a pylorus ligature and 100 mg/kg of acetylsalicyclic acid, (administered orally) is shown in table II.

TABLE II

The antiulcerogenic action and toxicity of benzodiazepinones

| Serial No. | Toxicity $LD_{50}$ [mg/kg] administered intravenously to mice | Protective action on the stomach $ED_{50}$ [mg/kg] administered perorally to rats | TQ $LD_{50}/ED_{50}$ | % inhibition of stomach secretion* in rats volume | % inhibition of stomach secretion* in rats hydrochloric acid |
|---|---|---|---|---|---|
| 1 | 290 | ~70 | ~4.1 | 7 | 4 |
| 2 | 180 | 12 | 15 | 10 | 5 |
| 3 | 95 | 9 | 10.5 | 7 | — |
| 4 | 160 | ~8 | ~20 | 32 | 22 |
| 5 | | <10 | | | |

$ED_{50}$ = the dose which reduces the ulcer index for the group treated by 50% compared with the control group
$LD_{50}$ = the dose at which 50% of the animals die
TQ = the therapeutic quotient $LD_{50}/ED_{50}$
*% inhibition = inhibition (in %) of stomach secretion 4 hours after administration of the antiulcerogenic $ED_{50}$ It should be emphasized particularly that, although an $ED_{50}$ can still be determined from compound 1, the dose/action curve then flattens out very considerably so that, even at 300 mg/kg, it is not possible to achieve any substantial increase in the anti-ulcerogenic action. In contrast to this, the action of compounds 2 to 5 depends strictly on the dose; inhibitory effects of up to 100% (30 mg/kg, substance 5) are achieved.

The anti-ulcerogenic action is tested by a method using the so-caled Shay rats:

Ulcers are provoked in rats which have been starved for 24 hours (female rats, 180 to 200 g, 4 animals in a cage with a high grille) by means of a pylorus ligature (under anaesthesia with diethyl ether) and oral administration of 100 mg/10 ml/kg of acetylsalicylic acid. The substances to be tested are administered orally (10 ml/kg) 1 hour before the pylorus ligature. The closure of the wound is effected by means of Michel's clips. The animals are killed 4 hours afterwards under ether anaesthesia by dislocating the atlas, and the stomach is cut out. The stomach is opened longitudinally and is fixed on a cork slab, the quantity of gastric juice secreted (volume) and the hydrochloric acid content having been determined beforehand; the number and size (= diameter) of ulcers present are determined by means of a stereomicroscope at a 10-fold magnification. The product of the degree of severity (in accordance with the following rating scale) and the number of the ulcers is used as an individual ulcer index.

| Point rating: | | |
|---|---|---|
| no ulcers | | 0 |
| ulcer diameter | 0.1–1.4 mm | 1 |
| | 1.5–2.4 mm | 2 |
| | 2.5–3.4 mm | 3 |
| | 3.5–4.4 mm | 4 |
| | 4.5–5.4 mm | 5 |
| | >5.5 mm | 6 |

The reduction in the average ulcer index in each group treated compared with that of the control group (=100%) is used as a measure of the anti-ulcerogenic effect. The $ED_{50}$ indicates the dose which reduces the average ulcer index by 50%.

Determination of toxicity

The toxicity investigations are carried out on female NMRI mice (body weight 22 to 26 g). The animals (5 animals per dose) receive feed and water ad lib. Various doses of the substances are administered intravenously (duration of injection 1 minute). The observation period is 7 days. The $LD_{50}$ (the dose at which 50% of the animals die) is determined by means of a linear regression.

The invention and its advantages are readily understood from the preceding description. Various changes may be made in the synthesis, the intermediates, the pharmacologically-active final products, the dosage forms, the medicament compositions and the mode of administration without departing from the spirit and scope of the invention or sacrificing its material advantages. The hereinbefore described aspects of the subject invention are merely illustrative of preferred embodiments.

What is claimed is:

1. A compound of the formula

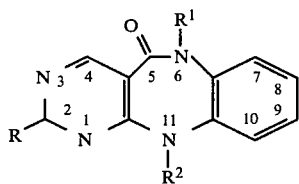

wherein
R is —H or phenyl,
$R^1$ is —H or alkyl with from 1 to 4 carbon atoms,
$R^2$ is —CO—$C_nH_{2n}$—$R^3$ or (when R is phenyl) —H,
$R^3$ is halo or —N($R^4$)$R^5$,
$R^4$ is alkyl with from 1 to 4 carbon atoms or alkenyl with from 3 to 5 carbon atoms,
$R^5$ is alkyl with from 1 to 4 carbon atoms and optionally substituted by dialkylamino with from 1 to 4 carbon atoms in each alkyl, or alkenyl with from 3 to 5 carbon atoms or
$R^4$ and $R^5$, together with the nitrogen atom to which both are bound, are pyrrolidino, piperidino, morpholino, perhydroazepino, piperazino which is optionally substituted in the 4-position by a methyl, ethyl or benzyl group, or homopiperazino which is optionally substituted in the 4-position by methyl, and
n is 1 or 2,
or an N-oxide or an acid-addition salt (with an inorganic or organic acid) thereof.

2. A compound according to claim 1, wherein
R is phenyl,
$R^1$ is —H or alkyl with from 1 to 4 carbon atoms,
$R^2$ is —CO—$C_nH_{2n}$—$R^3$,
$R^3$ is —N($R^4$)$R^5$,
$R^4$ is alkyl with from 1 to 4 carbon atoms or alkenyl with from 3 to 5 carbon atoms,
$R^5$ is alkyl with from 1 to 4 carbon atoms and optionally substituted by dialkylamino with from 1 to 4 carbon atoms in each alkyl, or alkenyl with from 3 to 5 carbon atoms or
$R^4$ and $R^5$, together with the nitrogen atom to which both are bound, are pyrrolidino, piperidino, morpholino, perhydroazepino, piperazino which is optionally substituted in the 4-position by a methyl, ethyl or benzyl group, or homopiperazino which is optionally substituted in the 4-position by methyl, and
n is 1 or 2,
or an N-oxide or an acid-addition salt (with an inorganic or organic acid) thereof.

3. A compound according to claim 2, wherein $R^1$ is alkyl with from 1 to 4 carbon atoms, $R^4$ is alkyl with from 1 to 4 carbon atoms, $R^5$ is alkyl with from 1 to 4 carbon atoms and substituted by dialkylamino with from 1 to 4 carbon atoms in each alkyl, or $R^4$ and $R^5$, together with the nitrogen atom to which each is bound, are pyrrolidino, piperidino, morpholino, or piperazino which is substituted in the 4-position by methyl, and n is 1, or a pharmacologically-compatible acid-addition salt thereof.

4. A compound according to claim 2, wherein $R^1$ is methyl, propyl, isopropyl, n-butyl or sec.-butyl, $R^4$ is methyl, $R^5$ is 2-dimethylaminoethyl, or $R^4$ and $R^5$, together with the nitrogen atom to which both are bound, are pyrrolidino, piperidino or N-methylpiperazino, and n is 1, or a pharmacologically-compatible acid-addition salt thereof.

5. A compound according to claim 4, which is 6-methyl-11-[(4-methyl-1-piperazinyl)acetyl]-2-phenyl-5,6-dihydropyrimido[4,5-b][1,5]benzodiazepin-5-one or a pharmacologically-compatible acid-addition salt thereof.

6. A compound according to claim 4, which is 6-methyl-2-phenyl-11-piperidino-acetyl-5,6-dihydropyrimido[4,5-b]-[1,5]-benzodiazepin-5-one or a pharmacologically-compatible acid-addition salt thereof.

7. A compound according to claim 4, which is 11-[N-(2-dimethylaminoethyl-N-methylamino)acetyl]-6-methyl-2-phenyl-5,6-dihydropyrimido[4,5-b][1,5]-benzodiazepin-5-one or a pharmacologically-compatible acid-addition salt thereof.

8. A compound according to claim 1, wherein
R is phenyl,
$R^1$ is —H or alkyl with from 1 to 4 carbon atoms,
$R^2$ is —H or —CO—$C_nH_{2n}$—$R^3$,
$R^3$ is halo, and
n is 1 or 2,
or an N-oxide or an acid-addition salt (with an inorganic or organic acid) thereof.

9. A compound according to claim 8, wherein $R^1$ is alkyl with from 1 to 4 carbon atoms, $R^3$ is chloro or bromo and n is 1, or an acid-addition salt thereof.

10. A compound according to claim 8, wherein $R^1$ is methyl, propyl, isopropyl, n-butyl or sec.-butyl, $R^3$ is chloro and n is 1, or an acid-addition salt thereof.

11. A compound according to claim 10, which is 11-chloro-acetyl-6-methyl-2-phenyl-5,6-dihydropyrimido[4,5-b][1,5]-benzodiazepin-5-one, or an acid-addition salt thereof.

12. A compound according to claim 10, which is 6-methyl-2-phenyl-5,6-dihydropyrimido[4,5-b][1,5]-benzodiazepin-5-one or an acid-addition salt thereof.

13. A compound according to claim 1, wherein
R is —H,
$R^1$ is —H or alkyl with from 1 to 4 carbon atoms,
$R^2$ is —CO—$C_nH_{2n}$—$R^3$,
$R^3$ is —N($R^4$)$R^5$,
$R^4$ is alkyl with from 1 to 4 carbon atoms or alkenyl with from 3 to 5 carbon atoms,
$R^5$ is alkyl with from 1 to 4 carbon atoms and optionally substituted by dialkylamino with from 1 to 4 carbon atoms in each alkyl, or alkenyl with from 3 to 5 carbon atoms or
$R^4$ and $R^5$, together with the nitrogen atom to which both are bound, are pyrrolidino, piperidino, morpholino, perhydroazepino, piperazino which is optionally substituted in the 4-position by a methyl, ethyl or benzyl group, or homopiperazino which is optionally substituted in the 4-position by methyl, and n is 1 or 2, or an N-oxide or an acid-addition salt (with an inorganic or organic acid) thereof.

14. A compound according to claim 13, wherein $R^4$ and $R^5$, together with the nitrogen atom to which both are bound, are pyrrolidino, piperidino, morpholino or piperazino which is substituted in the 4-position by methyl, and n is 1, or a pharmacologically-compatible acid-addition salt thereof.

15. A comound according to claim 13, wherein $R^1$ is —H, methyl or n-butyl, $R^4$ and $R^5$, together with the nitrogen atom to which both are bound, are piperidino, morpholino or N-methylpiperazino, and n is 1, or a pharmacologically-compatible acid-addition salt thereof.

16. A compound according to claim 15 which is 11-[(4-methyl-1-piperazinyl)acetyl]-5,6-dihydropyrimido[4,5-b][1,5]benzodiazepin-5-one, or a pharmacologically-compatible acid-addition salt thereof.

17. A compound according to claim 1, wherein

R is —H, $R^1$ is —H or alkyl with from 1 to 4 carbon atoms, $R^2$ is —CO—$C_nH_{2n}$—$R^3$, $R^3$ is halo, and n is 1 or 2, or an N-oxide or an acid-addition salt (with an inorganic or organic acid) thereof.

18. A compound according to claim 17, wherein $R^3$ is chloro or bromo, and n is 1, or an acid-addition salt thereof.

19. A compound according to claim 17, wherein $R^1$ is —H, methyl or n-butyl, $R^3$ is chloro, and n is 1, or an acid-addition salt thereof.

20. A compound according to claim 19, which is 11-chloroacetyl-5,6-dihydropyrimido[4,5-b][1,5]benzodiazepin-5-one, or an acid-addition salt thereof.

21. A pharmacologically-acceptable compound according to claim 1.

22. A compound according to claim 1 which is a free base or an N-oxide thereof.

23. A compound according to claim 1 which is a pharmacologically-acceptable acid-addition salt.

24. A pharmaceutical composition useful for the treatment and prophylaxis of of disease due to an affection of the stomach or intestines having pharmacologically-active principle and therapeutically-acceptable substantially-inert carrier and/or excipient, and wherein the active principle comprises from 0.5 to 95 percent by weight of the composition and from 1 to 300 milligrams of a pharmacologically-acceptable compound according to claim 1.

25. A method for the treatment and prophylaxis of disease due to an affection of the stomach or intestines which comprises administering to a mammal so inflicted an effective amount of a pharmacologically-acceptable compound according to claim 1.

* * * * *

UNITED STATES PATENT AND TRADEMARK OFFICE
CERTIFICATE OF CORRECTION

PATENT NO. : 4,311,700

DATED : January 19, 1982

INVENTOR(S) : Hartmann SCHAEFER

Page 1 of 2

It is certified that error appears in the above-identified patent and that said Letters Patent are hereby corrected as shown below:

Title page, at [54], "PYRIMIDOBENZODIAZEPINONES" should read --BENZODIAZEPIN-ONES--. Column 1, line 55, "[1,5]-ben-" should read --[1,5]ben- --. Column 2, line 9, in the formula, "$R_2$" should read --$R^2$--. Column 4, line 57, "1," should read --1;--. Column 5, line 50, "dropyrimido-" should read --dropyrimido--. Column 9, line 67, "h" should read --H--. Column 10, line 19, "organize" should read --organic--. Column 11, line 23, "repectively" should read --respectively--. Column 12, line 46, "36" should read --*36*--. Column 17, line 11, "-ethylamine" should read --ethylamine--. Column 18, line 46, "(tert.butyl)-" should read --(tert.-butyl)}--; line 47, "2-phenyl" should read --2-phenyl- --; line 52, "butyl)-amine" should read --butyl)amine--; line 60, "[{4-Methyl" should read --[(4-Methyl--. Column 19, line 24, "dihydropyrimido-" should read --dihydropyrimido--; line 63, "di-n-butylaminoacetyl" should read --di-(n-butyl)aminoacetyl--. Column 20, line 22, "Homopiperazinyl-acetyl" should read --Homopiperazinylacetyl--; line 65, "(bromopropionyl)-" should read --(bromopropionyl)]- --. Column 23, line 48, "one 6.8 g (23" should read --one--; line 49, "mmol) of" should read --6.8 g (23 mmol) of--. Column 24, line 4, "1968" should read --*1968*--; line 28, "6-isopropyl" should read --6-Isopropyl--. Column 25, line 58, "2-sec.-butyl-" should read --2-(sec.-butyl)--. Column 26, line 32, "-2-:" should read -- -2- --. Column 27, line 32, "anao-" should read --analo- --; line 34, "[1,5-" should read --[1,5]- --; line 42, "[4,59-b]" should read --[4,5-b]--; line 54, "dihydroxypyrimido" should read --dihydropyrimido--. Column 28, line 32, "benodiazepin" should read --benzodiazepin--; line 45, "phenyl5" should read --phenyl-5--; line 61, "dropyridmido" should read --dropyrimido--. Column 29, line 59, "piperidoactyl" should read --piperidinoacetyl--. Column 30, line 18, "*%" should read --*)%--; line 21, "from" should read --for--; line 30, "caled" should read --called--. Column 32, line 27, "[1,5]-" should read --[1,5]--; line 32, "[1,5]-" should read --[1,5]--. Column 33, line 16, "comound" should read --compound--.

UNITED STATES PATENT AND TRADEMARK OFFICE
CERTIFICATE OF CORRECTION

PATENT NO. : 4,311,700
DATED : January 19, 1982
INVENTOR(S) : Hartmann SCHAEFER

It is certified that error appears in the above-identified patent and that said Letters Patent are hereby corrected as shown below:

Column 2, line 5, and column 31, line 25, in the formula of each:

" 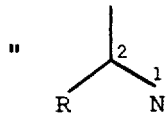 " should read -- 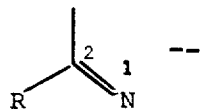 --

[SEAL]

Attest:

Attesting Officer

Signed and Sealed this

Fifth Day of April 1983

GERALD J. MOSSINGHOFF

Commissioner of Patents and Trademarks